US006939958B1

(12) United States Patent
Simmonds et al.

(10) Patent No.: US 6,939,958 B1
(45) Date of Patent: Sep. 6, 2005

(54) REGULATORY REGION OF A LIPID TRANSFER PROTEIN (LTPW1) FROM ALEURON TISSUE OF WHEAT

(75) Inventors: John Simmonds, Ontario (CA); Leslie Cass, Ontario (CA); Linda Harris, Ontario (CA); Sharon Allard, Ontario (CA); Kamal Malik, Ontario (CA); Teresa Martin-Heller, Ontario (CA); Dan Brown, Ontario (CA); Ming Hu, Ontario (CA); Brian Miki, Ontario (CA); Keqiang Wu, Morgantown, WV (US)

(73) Assignee: Her Majesty the Queen in Right of Canada, as represented by the Minister of Agriculture and Agri-Food, Ottawa (CA)

( * ) Notice: Subject to any disclaimer, the term of this patent is extended or adjusted under 35 U.S.C. 154(b) by 237 days.

(21) Appl. No.: 10/110,637

(22) PCT Filed: Oct. 13, 2000

(86) PCT No.: PCT/CA00/01185

§ 371 (c)(1),
(2), (4) Date: Jul. 25, 2002

(87) PCT Pub. No.: WO01/27296

PCT Pub. Date: Apr. 19, 2001

Related U.S. Application Data

(63) Continuation-in-part of application No. 09/417,777, filed on Oct. 14, 1999, which is a continuation-in-part of application No. 09/102,046, filed on Jun. 22, 1998, now Pat. No. 6,013,862.

(30) Foreign Application Priority Data

May 7, 1998 (CA) .............................................. 2230975

(51) Int. Cl.⁷ .............................................. C07H 21/04

(52) U.S. Cl. .................. 536/24.1; 536/23.1; 435/320.1; 435/419

(58) Field of Search .............................. 435/419, 320.1; 536/23.1, 24.1

(56) References Cited

U.S. PATENT DOCUMENTS

| 5,525,716 A | 6/1996 | Olsen et al. |
| 6,013,862 A | 1/2000 | Simmonds et al. |
| 6,326,528 B1 | 12/2001 | Simmonds et al. |

FOREIGN PATENT DOCUMENTS

| CA | 2110772 | 6/1995 |
| CA | 2 230 975 | 11/1999 |
| WO | WO 95 15389 | 6/1995 |
| WO | WO 95 23230 | 8/1995 |

OTHER PUBLICATIONS

Jakobsen et al., 1989, Plant Molecular Biology, 12:285–293.

(Continued)

*Primary Examiner*—James Ketter
*Assistant Examiner*—Konstantina Katcheves
(74) *Attorney, Agent, or Firm*—Morgan, Lewis & Bockius LLP

(57) ABSTRACT

This invention is directed to a regulatory region obtained from a wheat aleurone gene LtpW1. This regulatory region, truncated derivatives, mutations, or deletions of this regulatory region, can be used to express heterologous genes of interest within aleurone cells of a plant. Furthermore, this invention is directed to a truncated LtpW1 regulatory region that exhibits constitutive activity with both monocot and dicot plants. This invention is also directed to vectors comprising these regulatory regions operatively linked with a heterologous gene of interest, as well as plant cell cultures and transgenic plants comprising these vectors. A method for the preparation of a plant using the regulatory regions of this invention are also disclosed.

17 Claims, 18 Drawing Sheets

OTHER PUBLICATIONS

Kalla et al., 1994, Plant Journal, 6(6): 849.860.
Kim et al., Plant Mol. Biol., 24:105–117.
Leah et al., 1994, Plant J., 6(4):579–589.
Linnestad et al., 1991. Plant Physiol., 97:841–843.
McElroy et al., 1990. The Plant Cell, 2:163–171.
Molina et al., 1993, The Plant Journal, 4(6):983–991.
Odell et al., 1985, Nature, 313:810–812.
Skriver et al., 1992, Plant Molecular Biology, 19:585–589.
International Search Report dated Mar. 7, 2001.

*SEQ ID NO:1 (687 bp) >
-688 TCTAGAGAAAGAGTTTTAGACCGGAGGTATTTGTTAGGAAGTACTTCTTGCCATACTAGT

-628 TTCAATAAAGTAGCTTGAAAAGACATTTGTTAAGCAACCATGTGTTTTTAATATGAAGAT

-568 CCTCAATACCGAGAGCCTTTGGTCCCATGGATGACACAAAACTTCCCACTTGTTTTTTTT
 *SEQ ID NO:2 (473 bp) >
-508 TTTTGTGTGTGTGTGGGTAAACTTCCCACTTGGTTAACCTATACTTCCGCTTATGTTCAT

-448 CACTTTGCCAGAAAATTGCATATGTGAAGGAAGTGCCAATATTTAATACCGTCTGGTGTT

-388 ATAAATTCATCTCCCAAAATTATTGGAGTTGAAGATTCACTTGAAAAAATAATTTGACAT

-328 ATTAAAGATGTTGCCCTTGCGCGGGGTATCTGCAAATTGAGGATCCAAGGGACGATTGCA

-268 TCCAGTTCTAAACACACCATTATGATTTCAGTGATAATGCATGCTT*CCAAA*GCCCAGCTG
 *SEQ ID NO:3 (206 bp) >
-208 CAAGCTTGGGCCATCCTTCGGAAGGGAAAAAGAAAAAGGGGTCCTGCTGCACCAGCGACT

-148 AAACCATCCACGCATCTCTCGCTCGAACCCC*TATTTAA*GCCCCTCCATTCTTCCCTACAT

-88 TCTCC*ACACAA*CCACGAGTTGCTCATCTCTCCACCCAATCATCACTAGCTAATACGGTGC
                                                       +1
-28 ACTGTTAGCTACAGACCAAGAAGTGATCATGGCCCGCGCTCAGGTAATGCTCATGGCCGT

33 CGCCTTGGTGCTCATGCTCGCGGCGGTCCCGCGCGCTGCCGTGGCCATCGACTGCGGCCA

93 CGTTGACAGCTTGGTGAGACCCTGCCTGAGCTACGTTCAGGGCGGCCCCGGCCCGTCTGG

153 GCAGTGCTGCGACGGCGTCAAGAACCTCCATAACCAGGCGCGATCCCAGAGCGATCGCCA

213 AAGCGCTTGCAACTGCCTCAAGGGGATCGCTCGTGGCATCCACAATCTCAACGAGGACAA

273 CGCCCGCAGCATCCCCCCAAGTGCGGTGTCAACCTCCCATACACCATCAGTCTCAACAT

333 CGACTGCAGCAGGTGATTAATTCACATGCAAGCATATATATATGAACACTCATCCACGTA

393 AAATTTATTGATATTAACATTAATCAAATCTTTGCACTGCAGGGTGTAATGGGCGACGAT

453 CCGTCAAGCTGGTGCTCAGCTCATCCATCCACGTGGAGTTGAAGCGCGCAGCCTCTATCC

513 CTATGTAGTATGGTCACTAGTTATGCGAGTTTATACTGAATATGAATAAGAACTCTCTCC

573 AGCTGGCTTGCTGGTACTCCTCTGGAGGAGATCAGTATCTGTGTACCTGAGAGTTGAGAG

633 TTTGTACCATGGGCACTCCCAGTGTTTATGGACTTTAATACATACAACTCGTTCTGTTCA

693 GCGTGTGACTTATCTTTGTTTCCTCACGTTCGCCTGTCATATACTCCTTCCATCCGGTAT

753 TAGTTGGCGTTCAAACGGATATATCTAGA

FIGURE 3

```
-679  GTTTTAGACCGGAGGTATTTGTTAGGAAGTACTTCTTGCCATACTAGTTTCAATAAAGTA
      ||||  | |   ||   |       | |  |         | |      |       |||
-700  GTTTGATAACAAAGTAGTAAAAAAACTAAAGTATTAAAAACTGCAGTAATTTTACGTGTA

-619  GCTTGAAAAGACATTTGTTAAGCAACCATGTGTTTTAATATGAAGATCCTCAATACCGA
      |  ||||||| ||  | |||     |  ||  ||||   |  |       |  |  || ||
-630  GATAGAAAATACCATGGTTTTAATATAATAATATTTTTTGCAGTATTCACAATGTAGAGA

-559  GAGCCTTTGGTCCCATGGATGACACAAAACT..........................
       |  ||||  |  |        |
-570  AACTGTTTGATTACGCCACATATTACTGCAGTTTAGATCGAGCAAGTACACGGGAAGAAG

-528  .........TCCCACTTGTTTTTTTTTTTGTGTGTGTGTGGGTAAACTTCCCACTTGGT
               ||||||  || ||||     |         | |    |||   |     | |
-510  ATAACGACGTCCCACCCCTTCTTTTCGCCTTCTCTGTTTTTAAAAGAGGTCTGGGGTT

-477  TAACCTATACTTCCGCTTATGTTCATCACTTTGCCAGAAAATTGCATATGTGAAGGAAGT
      |    |  |     |   | || |   |        | ||  |     |     |   | |
-450  AGTTTTTTCAATACTGCAGTTTTAAAATCACAATTCTTAGAGGCAACCAAACACCTCATT

-417  GCCAATATTTAATACCGTCTGGTGTTATAAATTCATCTCCCAAAATTATTGGAGTTGAAG
      |  ||||         |           |         ||  |||||   |
-390  GTAAATAAAACTATGATAATCTCCAAAACTGCAGTATTCTAAAAATACTAC.........

-357  ATTCACTTGAAAAAATAATTTGACATATTAAAGATGTTGCCCTTGCGCGGGTATCTGCA
            ||||||   ||||  ||   |||      |                       |  ||
-339  ..........AAAAATTCTTTGTTATCAAACAGGGCCTAAGGAGTTAAAAAAATTAGCC

-297  AATTGAGGATCCAAGGGACGATTGCATC.....CAGTTCTAAACACACCATTATGATTTC
          |    |  || |            ||||   |  |||||        ||||
-289  GTAACTGAGACTCGGCGAGGCACCAGCAGCTAGCAGTCATCAACACT......TGATGGT
                                                         *SEQ ID NO:3 >
-242  AGTGATAATGCATGCTTCCAAAGCCCAGCTGCAAGCTTGGGCCATCCTTCGGAAGGGAAA
       |  |    |  |    | |  |    |   | |  ||  |       | |  |
-235  TGGCAAAGGCCAGTCGACGTGTCGCGGGCTCGGCCTGAGCGGGAGATACAATCTGTTCT

-182  AAGAAAAAGGGGTCCTGCTGCACCAGCGACTAAACCATCCACGCATCTCTCGCTCGAACC
         ||   |||    ||  ||  ||||||||| ||||||  ||||||||||||||||||||
-175  CCAGTAACCCCGTCGATTTGGCCCGCCGACTAAAGCATCCAGGCATCTCTCGCTCGAACC

-122  CCTATTTAAGCCCCTCCATTCTTCCCTACATTCTCCACACAACCACGAGTTGCTCATCTC
      |||||||||||||||||||||| |||| ||||||||||||   ||||||||||||
-115  CCTATTTAAGCCCCTCCATTCCTCCCAACATTCTCCACACCTCCACGAGTTGC.......
                                                                  *
 -62  TCCACCCAATCATCACTAGCTAATACGGTGCACTGTTAGCTACAGACCAAGAAGTGATCA
              |||||||||||||| |||| ||||||||||||||||||||  ||||||||||||
 -53  .........TCATCACTAGCTAGTACGTTGTACTGTTAGCTACAGATTAAGAAGTGATCA

2  TGGCCCGCGCTCAGGTAATGCTCATGGCCGTCGCCTTGGTGCTCATGCTCGCGGCGGTCC
      ||||||||||||||||||| |||||||||||||| |||||||||| ||||||  |||| ||
   2  TGGCCCGCGCTCAGGTACTGCTCATGGCCGCCGCCTTGGTGCTGATGCTCACGGCGGCCC
```

FIGURE 4a

```
 62 CGCGCGCTGCCGTGGCCATCGACTGCGGCCACGTTGACAGCTTGGTGAGACCCTGCCTGA
    ||||||||||||||||| || |||||||||| |||||||| | ||| ||| |||||||
 62 CGCGCGCTGCCGTGGCCCTCAACTGCGGCCAGGTTGACAGCAAGATGAAACCTTGCCTGA

122 GCTACGTTCAGGGCGGCCCCGGCCCGTCTGGGCAGTGCTGCGACGGCGTCAAGAACCTCC
    |||||||||||||||||||||||||| || | ||||||| |||||||| | | ||||
122 CCTACGTTCAGGGCGGCCCCGGCCCGTCCGGCGAATGCTGCAACGGCGTCAGGGATCTCC

182 ATAACCAGGCGCGATCCCAGAGCGATCGCCAAAGCGCTTGCAACTGCCTCAAGGGGATCG
    |||||||||||| |||| | |||| |||||||| || |||||||||||||| ||||||||||
182 ATAACCAGGCGCAATCCTCGGGCGACCGCCAAACCGTTTGCAACTGCCTGAAGGGGATCG

242 CTCGTGGCATCCACAATCTCAACGAGGACAACGCCCGCAGCATCCCCCCCAAGTGCGGTG
    |||| ||||||||||||||||||   |||||||| |||||||| ||||||||| ||
242 CTCGCGGCATCCACAATCTCAACCTCAACAACGCCGCCAGCATCCCCTCCAAGTGCAATG

302 TCAACCTCCCATACACCATCAGTCTCAACATCGACTGCAGCAGGTGATTAATTCACATGC
    ||||| ||||||||||||||||| | | ||||||||||| |||||||||||| |
302 TCAACGTCCCATACACCATCAGCCCCGACATCGACTGCTCCAGGTGATTAAATTTACACT

362 AAGCATA........................TATATGAAC
    | |                             |||||| ||||
363 CATCCAGAGTGAAATCTTTAAAAAGAACTATATTTACGAACGGAGTGAGTATATAGGAAC

380 ACTCATCCACGTAAAATTTATTGATATTAACATTAATCAAATCTTTGCA.CTGCAGGGTG
    | |||||||||||||||| |||||||||||||||||||     |  ||||||| |
423 ATTCATCCACGTAAAATTTGTTGATATTAACATTAACACGCATGATTGACCTGCAGGATT

440 TAATGGGCGACGATCCGTCAAGCTGGTGCTCAGCTCATCCATCCACGTGGAGTTGAAGCG
    || || |||||||||||||||||||||||||||||||||||| |||||||||||| |||||||
483 TACTGAGCGACGATCCGTCAAGCTGGTGCTCAGCTCATCGATCCACGTGGAGCTGAAGCG

500 CGCAGCCTCTATCCCTATGTAGTATGGTCACTAGTTATG.CGAGTTTATACTGAATATGA
    ||||||||| |||||||||||||||| || ||||||| |||||||| ||||
543 CGCAGCCTCTGTCCCTATGTAGTATGGCTACCAGTTATGCCGAGTTTATGCTGA......

559 ATAAGAACTCTCTCCAGCTGGCTTGCTGGTACTCCTCTGGAGGAGATCAGTATCTGTGTA
    |||||||||||||||         |||||||| |||||||||||||||||||||| ||||
597 ATAAGAACTCTCTCCT............GTACTCCTTTGGAGGAGATCAGTATCTATGTA

619 CCTGAGAGTTGAGAGTTTGTACCATGGGCACTCCCAGTGTTTATGGACTT
    | |||||||||||||||||||||||| |||||||||||||||||||||||
645 CGTGAGAGTTGAGAGTTTGTACCATCGGCACTCCCAGTGTTTATGGACTA
```

FIGURE 4a1

```
-681 AAAGAGTTTTAGACCGGAGGTATTTGTTAGGAAGTACTTCTTGCCATACTAGT..TTCAA
      ||    |  || ||  ||  ||  ||         |||  |||||
-822 AACCGTGGCCTAAAAATAAGCCGATGAGGATAAATAAAATGTGGTGGTACAGTACTTCAA

-623 TAAAGTAGCTTGAAAAGACATTTGTTAAGCAACCATGTGTTTTTAATATGAAGATCCTCA
      |  |  ||  ||||   |  ||   |  |  |  | |                ||  |
-762 GAGGTTTACTCATCAAGAGGATGCTTTTCCGATGAGCTCTAGTAGTACATCGGACCTCAC

-563 ATACCGAGAGCCTTTGGTCCCATGGATGACACAAAACTTCCCACTTGTTTTTTTTTTTG
     |||||   |   |    ||    |||      |      |    ||||  |||  ||
-702 ATACCTCCATTGTGGTGAAATATTTTGTGCTCATTTAGTGATGGGTAAATTTTGTTTATG

-503 TGTGTGT..GTGGGTAAACTTCCCACTTGGTTAACCTATACTTCCGCTTATGTTCATCAC
       |  |  ||  |  |  |||   |  ||   |  ||    |   ||  |  |   ||
-642 TCACTCTAGGTTTTGACATTTCAGTTTTGCCACTCTTAGGTTTTGACAAATAATTTCCAT

-445 TTTGCC.....AGAAAATTGCATATGTAAGGAAGTGCCAATATTTAATACCGTCTGGTG
      |  ||       ||  |||  |||   |  |    |  | ||| |   ||    |||
-582 TCCGCGGCAAAAGCAAAACAATTTTATTTTACTTTTACCACTCTTAGCTTTCACAATGTA

-390 TTATAAATTCATCTCCCAAAATTATTGGAGTTGAAGATTCACTTGAAAAAATAATTTGAC
     | | ||||| |  |||  |||||  ||    ||          |  ||||||||  |  ||
-522 TCACAAATGCCACTCTAGAAATTC.TGTTTATGCCACAGAATGTGAAAAAAACACTCAC

-330 ATATTA......AAGATGTTGCCCTTGCGCGGGGTATCTGCAAATTGAGGATCCAAGGGA
       ||||     |||  ||||      |          ||| |  | ||                |
-463 TTATTTGAAGCCAAGGTGTTCATGGCATGGAAATGTGACATAAAGTAACGTTCGTGTATA

-276 CGATTGCATCCAGT...TCTAAACACACCATTATGATTTCAGTGATAATGCATGCTTCCA
      ||   ||         ||  ||||    |     |   |||         |   |   ||   |
-403 AGAAAAAATTGTACTCCTCGTAACAAGAGACGGAAACATCATGAGACAATCGCGTTTGGA
                    *SEQ ID NO:3 >
-219 AAGCCCAGCTGCAAGCTTGGGCCATCCTTCGGAAGGGAAAAAGAAAAAGGGGTCCTGCTG
     |  ||   || ||  ||||    || |        ||| ||            ||  |||         ||
-343 AGGCTTTGCATCACCTTTGGATGATGCGCATGAATGG..........AGTCGTCTGCTTG

-159 CACCAGCGACTAAACCATCCACGCATCTCTCGCTCGAACCCCTATTTAAGCCCCTCCATT
     |      |||  ||||   |  | ||   ||| | ||      | |   |   ||
-293 CTAGCCTTCGCCTACCGCCCACTGAGTCCGGGCGGCAACTACCATCGGCGAACGACCCAG

-99 CTTCCCTACATTCTCCACACAACCACGAGTTGCTCATCTCTCCACCCAATCATCACTAG.
      || |||   |   |||   ||   | | | |      || ||  |   |    ||
-233 CTGACCTCTACCGACCGGACTTGAATGCGCTACCTTCGTCAGCGACGATGGCCGCGTACG

.................................................
-173 CTGGCGACGTGCCCCCGCATGCATGGCGGCACATGGCGAGCTCAGACCGTGCGTGGCTGG

-40 ..........................CTAATACGGTGCACTGTTAGCTA
                                 ||  |  ||        |||| ||
-113 CTACAAATACGTACCCCGTGAGTGCCCTAGCTAGAAACTTACACCTGCAACTGCGAGAGC
```

FIGURE 4b

```
-17  CAGACCAAGAAGTGATCATG
     ||      ||  |||
-53  GAGCGTGTGA.GTGTAGCCGAGTAGATCACCGTACGACGACGACGAGGGGCATG
```

FIGURE 4b1 a) p687LtpW1-GUS
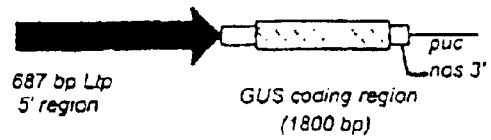
b) p473LtpW1-GUS
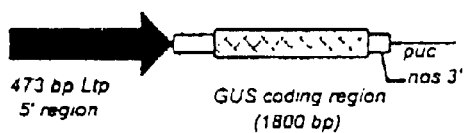
c) p206LtpW1-GUS
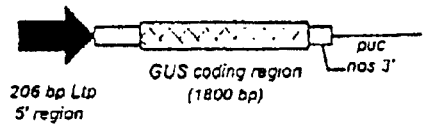
In all three constructs, the ADH1S6 intron lies between
The LtpW1 promoter and the GUS coding region.
d) pLC-GUS
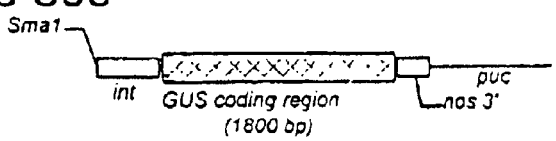
FIGURE 5 a) p35S-GUS
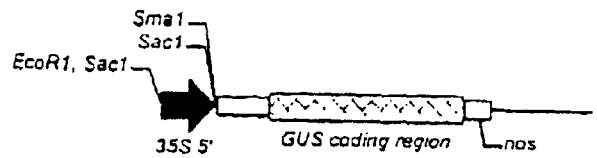
The ADH1S intron lies between the promoter and the GUS gene
b) pACT-GUS
FIGURE 6

FIGURE 13A
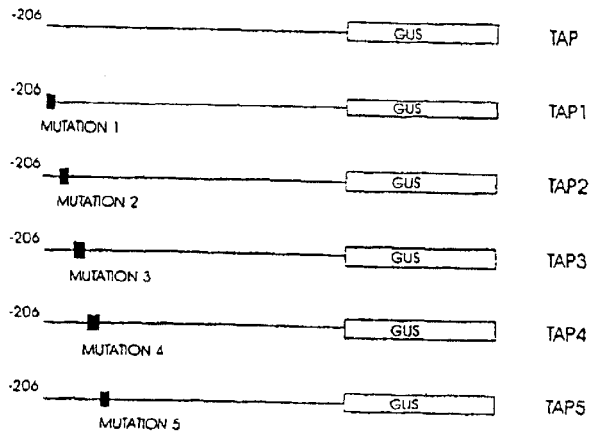
FIGURE 13B
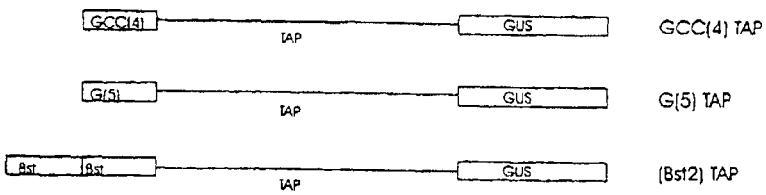
FIGURE 13C
```
     -206                                                          -148
     agcttgggcc atccttcgga agggaaaaag aaaaaggggt cctgctgcac cagcgactaa accatccacg
1.   ctaggatcca ------------------------------------------------------------------
2.   ----------- cgaaggatcc --------------------------------------------------------
3.   ---------------------- ggatcccct --------------------------------------------
4.   ------------------------------------ cccggatccg -----------------------------
5.   ---------------------------------------------------- aagtggatcc--------------
```

206 TAP.seq
caagcttggg ccatccttcg gaagggaaaa agaaaaaggg gtcctgctgc accagcgact
aaaccatcca cgcatctctc gctcgaaccc ctatttaagc ccctccattc ttccctacat
tctccacaca accacgagtt gctcatctct ccacccaatc atcactagct aatacggtgc
actgttagct acagaccaag aagtgatc 150 TAP
aaaccatcca cgcatctctc gctcgaaccc ctatttaagc ccctccattc ttccctacat
tctccacaca accacgagtt gctcatctct ccacccaatc atcactagct aatacggtgc
actgttagct acagaccaag aagtgatc 140 TAP
           cgcatctctc gctcgaaccc ctatttaagc ccctccattc ttccctacat
tctccacaca accacgagtt gctcatctct ccacccaatc atcactagct aatacggtgc
actgttagct acagaccaag aagtgatc 130 TAP
                      gctcgaaccc ctatttaagc ccctccattc ttccctacat
tctccacaca accacgagtt gctcatctct ccacccaatc atcactagct aatacggtgc
actgttagct acagaccaag aagtgatc 120 TAP
                                 ctatttaagc ccctccattc ttccctacat
tctccacaca accacgagtt gctcatctct ccacccaatc atcactagct aatacggtgc
actgttagct acagaccaag aagtgatc 110 TAP
                                            ccctccattc ttccctacat
tctccacaca accacgagtt gctcatctct ccacccaatc atcactagct aatacggtgc
actgttagct acagaccaag aagtgatc 100 TAP
                                                       ttccctacat
tctccacaca accacgagtt gctcatctct ccacccaatc atcactagct aatacggtgc
actgttagct acagaccaag aagtgatc 50 TAP
atcactagct aatacggtgc actgttagct acagaccaag aagtgatc 150 (-120 to -80 deletion)
aaaccatcca cgcatctctc gctcgaaccc *TGCAT*          accacgagtt gctcatctct
ccacccaatc atcactagct aatacggtgc actgttagct acagaccaag aagtgatc 150 (-130 to -120 / 113 -116 mutation)
aaaccatcca cgcatctctc gctcgaaccc *TGCATCA*   ctatAtaGgc ccctccattc
ttccctacat tctccacaca accacgagtt gctcatctct ccacccaatc atcactagct
aatacggtgc actgttagct acagaccaag aagtgatc Note: underline represents a PstI/NsiI fusion site, bold is mutations

FIGURE 13D

SEQUENCE LISTING

<160> NUMBER OF SEQ ID NOS: 39

<210> SEQ ID NO 1
<211> LENGTH: 687
<212> TYPE: DNA
<213> ORGANISM: Artificial Sequence
<220> FEATURE:
<223> OTHER INFORMATION: Description of Artificial Sequence:p687Ltp

<400> SEQUENCE: 1

```
ctagagaaag agttttagac cggaggtatt tgttaggaag tacttcttgc catactagtt      60
tcaataaagt agcttgaaaa gacatttgtt aagcaaccat gtgtttttaa tatgaagatc     120
ctcaataccg agagcctttg gtcccatgga tgacacaaaa cttcccactt gttttttttt     180
tttgtgtgtg tgtgggtaaa cttcccactt ggttaaccta tacttccgct tatgttcatc     240
actttgccag aaaattgcat atgtgaagga agtgccaata tttaataccg tctggtgtta     300
taaattcatc tcccaaaatt attggagttg aagattcact tgaaaaaata atttgacata     360
ttaaagatgt tgcccttgcg cggggtatct gcaaattgag gatccaaggg acgattgcat     420
ccagttctaa acacaccatt atgatttcag tgataatgca tgcttccaaa gcccagctgc     480
aagcttgggc catccttcgg aagggaaaaa gaaaaggggg tcctgctgca ccagcgacta     540
aaccatccac gcatctctcg ctcgaacccc tatttaagcc cctccattct tccctacatt     600
ctccacacaa ccacgagttg ctcatctctc cacccaatca tcactagcta atacggtgca     660
ctgttagcta cagaccaaga agtgatc                                         687
```

<210> SEQ ID NO 2
<211> LENGTH: 473
<212> TYPE: DNA
<213> ORGANISM: Artificial Sequence
<220> FEATURE:
<223> OTHER INFORMATION: Description of Artificial Sequence:0473Ltp

<400> SEQUENCE: 2

| | | | | | |
|---|---|---|---|---|---|
| aacctatact | tccgcttatg | ttcatcactt | tgccagaaaa | ttgcatatgt | gaaggaagtg | 60 |
| ccaatattta | ataccgtctg | gtgttataaa | ttcatctccc | aaaattattg | gagttgaaga | 120 |
| ttcacttgaa | aaataatttt | gacatattaa | agatgttgcc | cttgcgcggg | gtatctgcaa | 180 |
| attgaggatc | caagggacga | ttgcatccag | ttctaaacac | accattatga | tttcagtgat | 240 |
| aatgcatgct | tccaaagccc | agctgcaagc | ttgggccatc | cttcggaagg | gaaaagaaa | 300 |
| aagggtcct | gctgcaccag | cgactaaacc | atccacgcat | ctctcgctcg | aaccccctatt | 360 |
| taagcccctc | cattcttccc | tacattctcc | acacaaccac | gagttgctca | tctctccacc | 420 |
| caatcatcac | tagctaatac | ggtgcactgt | tagctacaga | ccaagaagtg | atc | 473 |

<210> SEQ ID NO 3
<211> LENGTH: 206
<212> TYPE: DNA
<213> ORGANISM: Artificial Sequence
<220> FEATURE:
<223> OTHER INFORMATION: Description of Artificial Sequence:p206Ltp

<400> SEQUENCE: 3

| | | | | | |
|---|---|---|---|---|---|
| agcttgggcc | atccttcgga | agggaaaaag | aaaaagggt | cctgctgcac | cagcgactaa | 60 |
| accatccacg | catctctcgc | tcgaacccct | atttaagccc | ctccattctt | ccctacattc | 120 |
| tccacacaac | cacgagttgc | tcatctctcc | acccaatcat | cactagctaa | tacggtgcac | 180 |
| tgttagctac | agaccaagaa | gtgatc | | | | 206 |

<210> SEQ ID NO 4
<211> LENGTH: 1469
<212> TYPE: DNA
<213> ORGANISM: Avena sp.

<400> SEQUENCE: 4

| | | | | | |
|---|---|---|---|---|---|
| tctagagaaa | gagttttaga | ccggaggtat | ttgttaggaa | gtacttcttg | ccatactagt | 60 |
| ttcaataaag | tagcttgaaa | agacatttgt | taagcaacca | tgtgttttta | atatgaagat | 120 |
| cctcaatacc | gagagccttt | ggtcccatgg | atgacacaaa | acttcccact | tgtttttttt | 180 |
| ttttgtgtgt | gtgtgggtaa | acttcccact | tggttaacct | atacttccgc | ttatgttcat | 240 |
| cactttgcca | gaaaattgca | tatgtgaagg | aagtgccaat | atttaatacc | gtctggtgtt | 300 |
| ataaattcat | ctcccaaaat | tattggagtt | gaagattcac | ttgaaaaaat | aatttgacat | 360 |
| attaaagatg | ttgcccttgc | gcggggtatc | tgcaaattga | ggatccaagg | gacgattgca | 420 |
| tccagttcta | aacacaccat | tatgatttca | gtgataatgc | atgcttccaa | agcccagctg | 480 |
| caagcttggg | ccatccttcg | gaagggaaaa | agaaaaaggg | gtcctgctgc | accagcgact | 540 |
| aaaccatcca | cgcatctctc | gctcgaaccc | ctatttaagc | cctccattc | ttccctacat | 600 |
| tctccacaca | accacgagtt | gctcatctct | ccacccaatc | atcactagct | aatacggtgc | 660 |
| actgttagct | acagaccaag | aagtgatcat | ggcccgcgct | caggtaatgc | tcatggccgt | 720 |
| cgccttggtg | ctcatgctcg | cggcggtccc | gcgcgctgcc | gtggcatcg | actgcggcca | 780 |

-continued

```
cgttgacagc ttggtgagac cctgcctgag ctacgttcag ggcggcccg gcccgtctgg      840 gcagtgctgc gacggcgtca agaacctcca taaccaggcg cgatcccaga gcgatcgcca      900
aagcgcttgc aactgcctca aggggatcgc tcgtggcatc cacaatctca acgaggacaa      960
cgcccgcagc atcccccca agtgcggtgt caacctccca tacaccatca gtctcaacat     1020
cgactgcagc aggtgattaa ttcacatgca agcatatata tatgaacact catccacgta     1080
aaatttattg atattaacat taatcaaatc tttgcactgc agggtgtaat gggcgacgat     1140
ccgtcaagct ggtgctcagc tcatccatcc acgtggagtt gaagcgcgca gcctctatcc     1200
ctatgtagta tggtcactag ttatgcgagt ttatactgaa tatgaataag aactctctcc     1260
agctggcttg ctggtactcc tctggaggag atcagtatct gtgtacctga gagttgagag     1320
tttgtaccat gggcactccc agtgtttatg gactttaata catacaactc gttctgttca     1380
gcgtgtgact tatctttgtt tcctcacgtt cgcctgtcat atactccttc catccggtat     1440
tagttggcgt tcaaacggat atatctaga                                      1469
```

<210> SEQ ID NO 5
<211> LENGTH: 148
<212> TYPE: DNA
<213> ORGANISM: Artificial Sequence
<220> FEATURE:
<223> OTHER INFORMATION: Description of Artificial Sequence: 150TAP

<400> SEQUENCE: 5

```
aaaccatcca cgcatctctc gctcgaaccc ctatttaagc ccctccattc ttccctacat       60
tctccacaca accacgagtt gctcatctct ccacccaatc atcactagct aatacggtgc      120
actgttagct acagaccaag aagtgatc                                        148
```

<210> SEQ ID NO 6
<211> LENGTH: 138
<212> TYPE: DNA
<213> ORGANISM: Artificial Sequence
<220> FEATURE:
<223> OTHER INFORMATION: Description of Artificial Sequence:140TAP

<400> SEQUENCE: 6

```
cgcatctctc gctcgaaccc ctatttaagc ccctccattc ttccctacat tctccacaca       60
accacgagtt gctcatctct ccacccaatc atcactagct aatacggtgc actgttagct      120
acagaccaag aagtgatc                                                    138
```

<210> SEQ ID NO 7
<211> LENGTH: 128
<212> TYPE: DNA
<213> ORGANISM: Artificial Sequence
<220> FEATURE:
<223> OTHER INFORMATION: Description of Artificial Sequence:130TAP

<400> SEQUENCE: 7

```
gctcgaaccc ctatttaagc ccctccattc ttccctacat tctccacaca accacgagtt       60
gctcatctct ccacccaatc atcactagct aatacggtgc actgttagct acagaccaag      120
aagtgatc                                                               128
```

<210> SEQ ID NO 8
<211> LENGTH: 118
<212> TYPE: DNA
<213> ORGANISM: Artificial Sequence
<220> FEATURE:
<223> OTHER INFORMATION: Description of Artificial Sequence:120TAP

<400> SEQUENCE: 8
ctatttaagc ccctccattc ttccctacat tctccacaca accacgagtt gctcatctct          60
ccacccaatc atcactagct aatacggtgc actgttagct acagaccaag aagtgatc           118

<210> SEQ ID NO 9
<211> LENGTH: 108
<212> TYPE: DNA
<213> ORGANISM: Artificial Sequence
<220> FEATURE:
<223> OTHER INFORMATION: Description of Artificial Sequence:110TAP

<400> SEQUENCE: 9
ccctccattc ttccctacat tctccacaca accacgagtt gctcatctct ccacccaatc          60
atcactagct aatacggtgc actgttagct acagaccaag aagtgatc                     108

<210> SEQ ID NO 10
<211> LENGTH: 98
<212> TYPE: DNA
<213> ORGANISM: Artificial Sequence
<220> FEATURE:
<223> OTHER INFORMATION: Description of Artificial Sequence:100TAP

<400> SEQUENCE: 10
ttccctacat tctccacaca accacgagtt gctcatctct ccacccaatc atcactagct          60
aatacggtgc actgttagct acagaccaag aagtgatc                                 98

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence:50TAP

<400> SEQUENCE: 11
atcactagct aatacggtgc actgttagct acagaccaag aagtgatc                      48

<210> SEQ ID NO 12
<211> LENGTH: 113
<212> TYPE: DNA
<213> ORGANISM: Artificial Sequence
<220> FEATURE:
<223> OTHER INFORMATION: Description of Artificial Sequence:120-80TAP

<400> SEQUENCE: 12
aaaccatcca cgcatctctc gctcgaaccc tgcataccac gagttgctca tctctccacc          60
caatcatcac tagctaatac ggtgcactgt tagctacaga ccaagaagtg atc               113

<210> SEQ ID NO 13
<211> LENGTH: 155
<212> TYPE: DNA
<213> ORGANISM: Artificial Sequence
<220> FEATURE:
<223> OTHER INFORMATION: Description of Artificial
      Sequence:130-120/133-116TAP

<400> SEQUENCE: 13
aaaccatcca cgcatctctc gctcgaaccc tgcatcacta tataggcccc tccattcttc          60
cctacattct ccacacaacc acgagttgct catctctcca cccaatcatc actagctaat         120
acggtgcact gttagctaca gaccaagaag tgatc                                   155

```
<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:Pr1 (for
      TAP1)

<400> SEQUENCE: 14
ctaggatcca atccttcgga agggaaaaag                                    30

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence:Pr2 (for
      TAP2)

<400> SEQUENCE: 15
agcttgggcc cgaaggatcc agggaaaaag aaaaagggggt c                      41

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence:Pr3 (for
      TAP3)

<400> SEQUENCE: 16
agcttgggcc atccttcgga ggatccccct aaaaagggggt cctgctgcac             50

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence:Pr4 (for
      TAP4)

<400> SEQUENCE: 17
agcttgggcc atccttcgga agggaaaaag cccggatccg cctgctgcac cagcgactaa   60

<210> SEQ ID NO 18
<211> LENGTH: 70
<212> TYPE: DNA
<213> ORGANISM: Artificial Sequence
<220> FEATURE:
<223> OTHER INFORMATION: Description of Artificial Sequence:Pr5 (for
      TAP5)

<400> SEQUENCE: 18
agcttgggcc atccttcgga agggaaaaag aaaaaggggt aagtggatcc cagcgactaa   60
accatccacg                                                          70

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:Pr6

<400> SEQUENCE: 19
ggtaccgtgt gcagcaggac ccctttttc                                     29
```

```
<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:Pr 7

<400> SEQUENCE: 20
cggaattcga aagcttgcat gcctgcagg                                29

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence:Pr 8

<400> SEQUENCE: 21
aattgagctc atgcatggat caaaagggga aac                           33

<210> SEQ ID NO 22
<211> LENGTH: 206
<212> TYPE: DNA
<213> ORGANISM: Artificial Sequence
<220> FEATURE:
<223> OTHER INFORMATION: Description of Artificial Sequence:TAP1

<400> SEQUENCE: 22
ctaggatcca atccttcgga agggaaaaag aaaaagggt cctgctgcac cagcgactaa    60
accatccacg catctctcgc tcgaacccct atttaagccc ctccattctt ccctacattc   120
tccacacaac cacgagttgc tcatctctcc acccaatcat cactagctaa tacggtgcac   180
tgttagctac agaccaagaa gtgatc                                       206

<210> SEQ ID NO 23
<211> LENGTH: 206
<212> TYPE: DNA
<213> ORGANISM: Artificial Sequence
<220> FEATURE:
<223> OTHER INFORMATION: Description of Artificial Sequence:TAP2

<400> SEQUENCE: 23
agcttgggcc cgaaggatcc agggaaaaag aaaaagggt cctgctgcac cagcgactaa    60
accatccacg catctctcgc tcgaacccct atttaagccc ctccattctt ccctacattc   120
tccacacaac cacgagttgc tcatctctcc acccaatcat cactagctaa tacggtgcac   180
tgttagctac agaccaagaa gtgatc                                       206

<210> SEQ ID NO 24
<211> LENGTH: 206
<212> TYPE: DNA
<213> ORGANISM: Artificial Sequence
<220> FEATURE:
<223> OTHER INFORMATION: Description of Artificial Sequence:TAP 3

<400> SEQUENCE: 24
agcttgggcc atccttcgga ggatcccct aaaaagggt cctgctgcac cagcgactaa     60
accatccacg catctctcgc tcgaacccct atttaagccc ctccattctt ccctacattc   120
tccacacaac cacgagttgc tcatctctcc acccaatcat cactagctaa tacggtgcac   180
tgttagctac agaccaagaa gtgatc                                       206

<210> SEQ ID NO 25
```

```
<211> LENGTH: 206
<212> TYPE: DNA
<213> ORGANISM: Artificial Sequence
<220> FEATURE:
<223> OTHER INFORMATION: Description of Artificial Sequence:TAP4

<400> SEQUENCE: 25
agcttgggcc atccttcgga agggaaaaag cccggatccg cctgctgcac cagcgactaa      60
accatccacg catctctcgc tcgaacccct atttaagccc ctccattctt ccctacattc     120
tccacacaac cacgagttgc tcatctctcc acccaatcat cactagctaa tacggtgcac     180
tgttagctac agaccaagaa gtgatc                                          206

<210> SEQ ID NO 26
<211> LENGTH: 206
<212> TYPE: DNA
<213> ORGANISM: Artificial Sequence
<220> FEATURE:
<223> OTHER INFORMATION: Description of Artificial Sequence:TAP5

<400> SEQUENCE: 26
agcttgggcc atccttcgga agggaaaaag aaaaaggggt aagtggatcc cagcgactaa      60
accatccacg catctctcgc tcgaacccct atttaagccc ctccattctt ccctacattc     120
tccacacaac cacgagttgc tcatctctcc acccaatcat cactagctaa tacggtgcac     180
tgttagctac agaccaagaa gtgatc                                          206

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence:TAP150
      primer

<400> SEQUENCE: 27
tttgaattcg gtacctccac gcatctctcg ctcg                                  34

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence:TAP140
      primer

<400> SEQUENCE: 28
tttgaattcg gtacccgcat ctctcgctcg aac                                   33

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence:TAP130
      primer

<400> SEQUENCE: 29
tttgaattcg gtaccgctcg aaccccctatt taa                                  33

<210> SEQ ID NO 30
<211> LENGTH: 32
<212> TYPE: DNA
<213> ORGANISM: Artificial Sequence
<220> FEATURE:
```

<223> OTHER INFORMATION: Description of Artificial Sequence::TAP120
      primer

<400> SEQUENCE: 30
tttgaattcg gtaccctatt taagcccctc cc                                    32

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence::TAP110
      primer

<400> SEQUENCE: 31
tttgaattca tgcatccctc cattcttccc tac                                   33

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence::TAP100
      primer

<400> SEQUENCE: 32
tttgaattcg gtaccttccc tacattctcc acacaacc                              38

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence::TAP50
      primer

<400> SEQUENCE: 33
tttgaattcg gtaccatcac tacgtaatac ggtgc                                 35

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:GUS AS

<400> SEQUENCE: 34
tcacgggttg ggggttctac                                                  20

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence:GUS AS - 11
      0TAP

<400> SEQUENCE: 35
ttgaattcat gcatcactat atagcccctc c                                     31

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:120TAP-M13

```
<400> SEQUENCE: 36
ttttctgcag gggttcgagc gagagatgcg                                        30

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence:GUS AS-80TAP

<400> SEQUENCE: 37
tttatgcata ccacgagttg ctcatctcc                                         29

<210> SEQ ID NO 38
<211> LENGTH: 46
<212> TYPE: DNA
<213> ORGANISM: Artificial Sequence
<220> FEATURE:
<223> OTHER INFORMATION: Description of Artificial Sequence:GCC(4)box

<400> SEQUENCE: 38
aattgccgcc actagccgcc gaccgagccg ccaagagccg ccagct                      46

<210> SEQ ID NO 39
<211> LENGTH: 54
<212> TYPE: DNA
<213> ORGANISM: Artificial Sequence
<220> FEATURE:
<223> OTHER INFORMATION: Description of Artificial Sequence:G(5) box

<400> SEQUENCE: 39
aattgccgcc acgtgccgcc acgtgccgcc acgtgccgcc acgtgccgcc agct             54
```

REGULATORY REGION OF A LIPID TRANSFER PROTEIN (LTPW1) FROM ALEURON TISSUE OF WHEAT

CROSS REFERENCE TO RELATED APPLICATIONS

This application is a 371 filing of PCT/CA00/01185, filed Oct. 13, 2000, which is a CIP of U.S. application Ser. No. 09/417,777, filed Oct. 14, 1999, which is a CIP of U.S. application Ser. No. 09/102,046, filed Jun. 22, 1998 now U.S. Pat. No. 6,013,862 which claims priority from Canadian application no. 2,230,975, filed May 7, 1998.

BACKGROUND OF THE INVENTION

The present invention relates to plant gene regulatory regions and their use in the expression of genes of interest. More specifically, the present invention relates to the use of an aleurone regulatory region for organ, and tissue specific expression of a gene of interest within aleurone tissues of plants, and for constitutive expression of a gene of interest within monocot and dicotyledonous plants. This invention also pertains to derivatives of the aleurone regulatory region and their activity in monocot and dicotyledonous plants.

The endosperm of a seed is the site of deposition of storage products such as starch and proteins used by the developing embryo during germination. The endosperm surrounds the embryo of developing and mature cereal seeds. The endosperm comprises a peripheral layer of aleurone cells, which are specialized secretory cells. During germination, the aleurone layer is involved in the transfer of metabolites from the transport system to the endosperm. Furthermore, several antimicrobial compounds required to protect the seed during dormancy, imbibition and germination are synthesized within this tissue. The aleurone cells differentiate from primary endosperm cells 10–21 days after fertilization.

Several aspects of hormonal regulation of gene transcription within aleurone tissue, in germinating barley seeds have been well characterized (Fincher 1989, Annu. Rev. Plant Physiol. Mol. Biol. 40: 305–346). For example, genes encoding α-amylase, responsible for the digestion of the starch stored within the starchy endosperm, and β-glucanase, which digests the cell walls, have been isolated and characterized (WO 90/01551 Rogers; U.S. Pat. No. 5,677,474 Rogers, issued Oct. 14, 1997; Karrer et al 1991, Plant Mol. Biol. 16: 797–805; Slakeski and Fincher 1992). Furthermore, several structural and regulatory genes involved in anthocyanin biosynthesis within the aleurone have been isolated and characterized (Paz-Ares et al 1987, EMBO J. 5: 829–833; Dellaporta et al 1988, pp 263–282 18th Stadler Genet. Symp. ed. J. P. Gustafsant and R. Appels). Other genes representing differentially expressed transcripts within aleurone layers have also been reported including CHI26 (Lea et al 1991, J. Biol. Chem. 266: 1564–73); pZE40 (Smith et al 1992, Plant Mol. Biol. 20: 255–66); pHvGS-1, and pcHth3 (Heck and Ho 1996, Plant Mol. Biol. 30: 611–23). Several genes encoding lipid transfer proteins (Ltp) have also been obtained from barley aleurone tissues, including B11E– barley Ltp1, and B12A– barley Ltp2 (Jakobsen et al 1989, Plant Mol. Biol. 12: 285–93). Only one of these genes, B12A, has been expressed ectopically in transgenic plants. In this case the promoter is active only during seed development (Kalla et al 1994 Plant J. 6: 849–860).

Lipid transfer proteins are responsible for the transfer of phospholipids between membranes in vitro, and likely play a role during membrane biogenesis. This may be especially important in aleurone cells which are known to develop extensive membrane systems. Skriver et al (1992, Plant Mol. Biol. 18: 585–589) disclose the sequence of a genomic Ltp (Ltp1), including the promoter region, from barley. Northern analysis demonstrated that this gene was specifically expressed in developing and germinating seeds, as well as in whole seeds and aleurone layers obtained from seeds 30 days post anthesis (dpa). No expression of Ltp1 mRNA was observed in root, leaf, or shoot tissues, or coleoptiles of germinating seeds. Linnestad et al (1991, Plant Physiol 97: 841–843) also discloses the promoter sequence of the Ltp1 promoter from barley which was obtained using barley cDNA B12A as a probe. The Ltp1 promoter, as well as a modified form of this promoter is disclosed in WO 95/23230 (Feb. 23, 1995; Olsen et al). The modified form of the Ltp1 promoter was not specific to directing expression within aleurone cells, and was active in a range of plant organs and tissues including aleurone cells, scutellar epithelial tissue and vascular tissue during germination or in the plant, including root, leaves and stem.

The promoter of B12A (also termed Ltp2) directs expression specifically within the aleurone layer of developing grain as determined using transgenic cereal plants (Kalla et al 1994, Plant J. 6: 849–860). The sequence of the Ltp2 promoter is disclosed in CA 2,110,772 (filed Dec. 6, 1993, Olsen and Kalla) and U.S. Pat. No. 5,525,716 (Kalla et al). Dieryck et al (1992, Plt,. Molec. Biol 19: 707–709) disclose the incomplete cDNA sequence of a wheat (*Triticum durum*) Ltp (pTd4.90). Ltp genes comprise a multigenic family and are ubiquitous in plants. Unfortunately as these genes or corresponding proteins have been isolated from various species there is no uniformity in the terminology used to identify the genes. Hence Ltp1 from tobacco, barley and *Arabidopsis* are not the same. As well, two barley Ltp2 genes are described in the literature; barley Lpt2 as described in Molina and Garcia-Olmedo (Plant J. 4: 983–991) is a leaf Lpt, while barley Ltp2 as described in Kalla et al (1994 Plant J. 6: 849–860) is aleurone specific.

It is desirable to provide regulatory regions capable of controlling aleurone specific expression that is not detrimental to the developing embryo and seedling. Aleurone-specific regulatory regions may be used for the regulation of the expression of heterologous or native genes within aleurone tissue of cereal seeds in order to modify grain development and germination. For example, placing genes of interest under the control of aleurone-specific regulatory regions may be used to:

1) mediate the unloading of metabolites from the transport system into the endosperm, since this metabolite unloading is processed through aleurone cells. By expressing genes of interest involved in this process specifically within the aleurone, the grain yield may be affected. For example, which is not to be considered limiting in any manner, these genes of interest may include $Na^+$ and $K^+$ ATPases functioning in active transport, modifiers of membrane pore exclusion parameters such as TMV movement proteins, invertase for sucrose transport etc.;

2) affect the quality of the grain, through the production of specific proteins or enzymes, lipids, secondary metabolites etc. and their secretion into the endosperm during endosperm development or endosperm digestion. For example, which is not to be considered limiting in any manner, such proteins may include starch synthase, ADP glucose pyrophosphorylase, monoclonal antibodies, glutenins, anticoagulants (eg hirudin), anti-pathogenic phenolics etc. Furthermore, expression of a gene of interest within the aleurone may also be used in order to express proteins for nutritional or medicinal purposes for feeding to animals or humans;

3) regulate pre-harvest sprouting by affecting dormancy, for example which is not to be considered limiting, by over-expression of ACC synthase to induce inhibitory levels of ethylene;

4) enhance alcohol production-introduction of novel high temperature resistant enzymes for industrial application, including, but not limited to, thermostable amylases, pectinases and invertase;

5) modify disease resistance of developing and germinating grains by expressing proteins, for example but not limited to, oxalate oxidase, glucose oxidase, chitinase, or lipid transfer proteins, in combination with a suitable signal peptide for targeting to the extracellular matrix and cell wall localization. This approach can be used to modify the matrix to provide a stronger physical barrier against invading pathogens or to direct specific anti-pathogen agents to the aleurone/pericarp interface.

This invention characterizes a novel wheat aleurone specific regulatory region active during embryo development and germination and which controls expression of heterologous genes of interest within transgenic plants. Furthermore, this invention relates to a constitutive regulatory element that is active within monocot and dicotyledonous plants, and which can be used to drive the expression of a gene of interest in a variety of plants.

SUMMARY OF THE INVENTION

The present invention relates to plant gene regulatory regions and their use in the expression of genes of interest. More specifically, the present invention relates to the use of a constitutive regulatory region and derivatives of this regulatory region for expression of a gene of interest within both monocotyledonous and dicotyledonous plants.

Accordingly, the present invention is directed to a regulatory element comprising, the nucleotide sequence of SEQ ID NO:3, or a fragment, mutation, or derivative thereof, or a nucleotide sequence that hybridizes to the nucleotide sequence of SEQ ID NO:3 under the following conditions: hybridization in 5×SSC and 50% formamide at 42° C.; and washing from about 0.5×SSC to about 0.2×SSC at 65° C., and exhibits regulatory element activity. Preferably, the regulatory element exhibits constitutive activity. Furthermore, the present invention includes the regulatory element as just defined wherein the regulatory element is a chimeric regulatory element, comprising an exogenous regulatory element selected from the group consisting of an enhancer element and a silencer element.

This invention also pertains to a vector comprising the regulatory element defined above in operative association with a gene of interest, and to a transformed plant cell culture, a transgenic plant, either monocotyledonous or dicotyledonous plant, or a transgenic seed comprising the vector as just defined.

The present invention also embraces a regulatory element comprising, a nucleotide sequence selected from the group consisting of SEQ ID NO's:5–11 and 22–26, or a fragment, mutation, or derivative thereof, or a nucleotide sequence that hybridizes to a nucleotide sequence selected from the group consisting of SEQ ID NO's: 5–11 and 22–26, under the following conditions: hybridization in 5×SSC and 50% formamide at 42° C.; and washing from about 0.5×SSC to about 0.2×SSC at 65° C., and that exhibits regulatory element activity.

This invention relates to a transgenic dicotyledonous plant comprising a gene construct, wherein the gene construct comprises:

i) a nucleotide sequence selected from the group consisting of SEQ ID NO's: 5–11 and 22–26, or a fragment, mutation, or derivative thereof, or a nucleotide sequence that hybridizes to a nucleotide sequence selected from the group consisting of SEQ ID NO's: 5–11 and 22–26, under the following conditions: hybridization in 5×SSC and 50% formamide at 42° C.; and washing from about 0.5×SSC to about 0.2×SSC at 65° C., and hat exhibits regulatory element activity; and ii) a gene of interest in operative association with said nucleotide sequence.

Furthermore, this invention includes a transgenic monocotyledonous plant comprising a gene construct comprising:

i) a nucleotide sequence selected from the group consisting of SEQ ID NO's: 5–11 and 22–26, or a fragment, mutation, or derivative thereof, or a nucleotide sequence that hybridizes to a nucleotide sequence selected from the group consisting of SEQ ID NO's: 5–11 and 22–26, under the following conditions: hybridization in 5×SSC and 50% formamide at 42° C.; and washing from about 0.5×SSC to about 0.2×SSC at 65° C., and that exhibits regulatory element activity; and ii) a gene of interest in operative association with said nucleotide sequence.

The present invention also considers a method of expressing a gene of interest within a plant comprising:

i) operatively linking a gene of interest for which expression is desired with the regulatory region of claim 1 to produce a gene construct; and ii) introducing said gene construct into said plant and allowing for expression of said gene of interest.

This method includes a plant that is a monocotyledonous plant, or a dicotyledonous plant.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1(*a*) shows *Hordeum vulgare* at 20 dpa; FIG. 1(*b*) shows *Triticum aestivum* at 10 dpa; FIG. 1(*c*) shows *T. aestivum* at 20 dpa; FIG. 1(*d*) shows *T. tungidum* at 10 dpa.

FIG. 2(*a*) and FIG. 2(*b*) show 73h germinating wheat grain, and FIG. 2(*c*) and FIG. 2(*d*) show 18 dpa developing wheat grain. FIG. 2(*a*) and FIG. 2(*c*) show hybridization results using anti-sense probe; FIG. 2(*b*) and FIG. 2(*d*) show hybridization with sense probe.

FIG. 3 shows the DNA sequence of the genomic LtpW1 gene. The coding region is underlined (the intron is not underlined). The ATG start and TGG stop codon are in bold type. The cap site, TATA, CAT boxes are italicized and double-underlined at positions −83, −117 and −222, respectively. SEQ ID NO 1 runs from −687 to −1, SEQ ID NO 2 runs from 473 to −1, and SEQ ID NO 3 runs from −206 to −1.

FIG. 4 shows the DNA sequence alignment of LtpW1 and barley Ltp genes. FIG. 4(a) shows alignment of LtpW1 (top row) and barley Ltp1 (bottom row); FIG. 4(b) shows alignment of LtpW1 (top row) and barley Ltp2 (Kalla et al 1994 Plant J. 6: 849–860). The ATG of the Ltp genes is overlined.

FIG. 5 shows the LtpW1 regulatory region constructs, in all three constructs the ADH1S6 intron lies between the LtpW1 regulatory region and the coding region of the marker gene, GUS. FIG. 5(a) p687LtpW1-GUS; FIG. 5(b) p473LtpW1-GUS; FIG. 5(c) p206LtpW1-GUS; FIG. 5(d) pLC-GUS, the promoterless control used in transient assays.

FIG. 6 shows two constructs used for comparative studies containing prior art promoters. FIG. 6(a) P35s-GUS, FIG. 6(b) pACT-GUS.

FIG. 7(a) shows *T. aestivum* at 15 dpa; FIG. 5(b) shows *Zea mays* at 13 dpa, and FIG. 7(c) shows *H. vulgare* at 12 dpa.

FIG. 12 shows a series of deletion constructs of the TAP (p206Ltp) regulatory region and there activity in corn.

FIG. 13 shows a series of mutational TAP constructs. FIG. 13(A) shows a diagrammatical representation of a mutational series TAP 1–TAP 5. FIG. 13(B) shows a diagrammatical representation of several chimeric TAP constructs, GCC(4) TAP, G(5) TAP and (Bst2) TAP. FIG. 13(C) shows the substituted nucleotides within the TAP1 to TAP 5 mutational series of FIG. 13(A). Substitutions 1–5 correspond to TAP 1 to TAP 5, respectively. FIG. 13(D) shows the nucleic acid sequence of the deletion series for FIG. 13(A).

FIG. 14 shows activity of several regulatory regions of the present invention.

DESCRIPTION OF PREFERRED EMBODIMENT

The present invention relates to plant gene regulatory regions and their use in the expression of genes of interest. More specifically, the present invention relates to the use of a consitutive regulatory region for expression of a gene of interest within plants.

The following description is of a preferred embodiment by way of example only and without limitation to the combination of features necessary for carrying the invention into effect.

Described below is a constitutive regulatory element p206LtpW1 (SEQ ID NO:3), that is active in both monocotyledonous and dicotyledonous plants. The constitutive regulatory element was obtained from a wheat genomic Ltp sequence termed LtpW1 (SEQ ID NO:4). The coding region of the LtpW1 gene sequence exhibits about an 85% homology with barley Ltp 1, and includes a 26 amino acid transit peptide. The regulatory region of a wheat lipid transfer protein (Ltp) gene, LtpW1, has been isolated and characterized. This regulatory region comprises a novel oligonucleotide sequence (SEQ ID NO: 1), which is active in aleurone of wheat, maize and barley. The full length regulatory region is not active in leaf, root, or coleoptile tissues. However, a truncated form of LtpW1 regulatory region, termed 206Ltp, 206LtpW1 or TAP (Truncated Aleurone Promoter; SEQ ID NO 3), is active in a range of tissues and plant organs, and is active in both monocot and dicot plants.

The regulatory region of LtpW1 compared to the barley Ltp1 regulatory region has 43% sequence similarity with the majority of sequence similarity (82%) occurring within 140 nucleotides upstream of the transcriptional start site (see FIG. 4(a)). A minor sequence similarity was noted between LtpW1 and a barley amylase protease inhibitor, however, no sequence similarity of any significance was observed between LtpW1 and Ltp2, or other known Ltp regulatory region sequences.

The full length LtpW1 regulatory region (687 nucleotides; p687LtpW1; SEQ ID NO:1), or a truncated LtpW1 regulatory region, p473LtpW1 (SEQ ID NO:2; comprising a 473 nucleotide fragment of the full length regulatory region), can be used to drive the expression of a gene of interest within the aleurone layer of a developing and germinating seed of a monocotyledonous plant, for example, but not limited to, wheat, rice, barley and maize.

Figure 7:
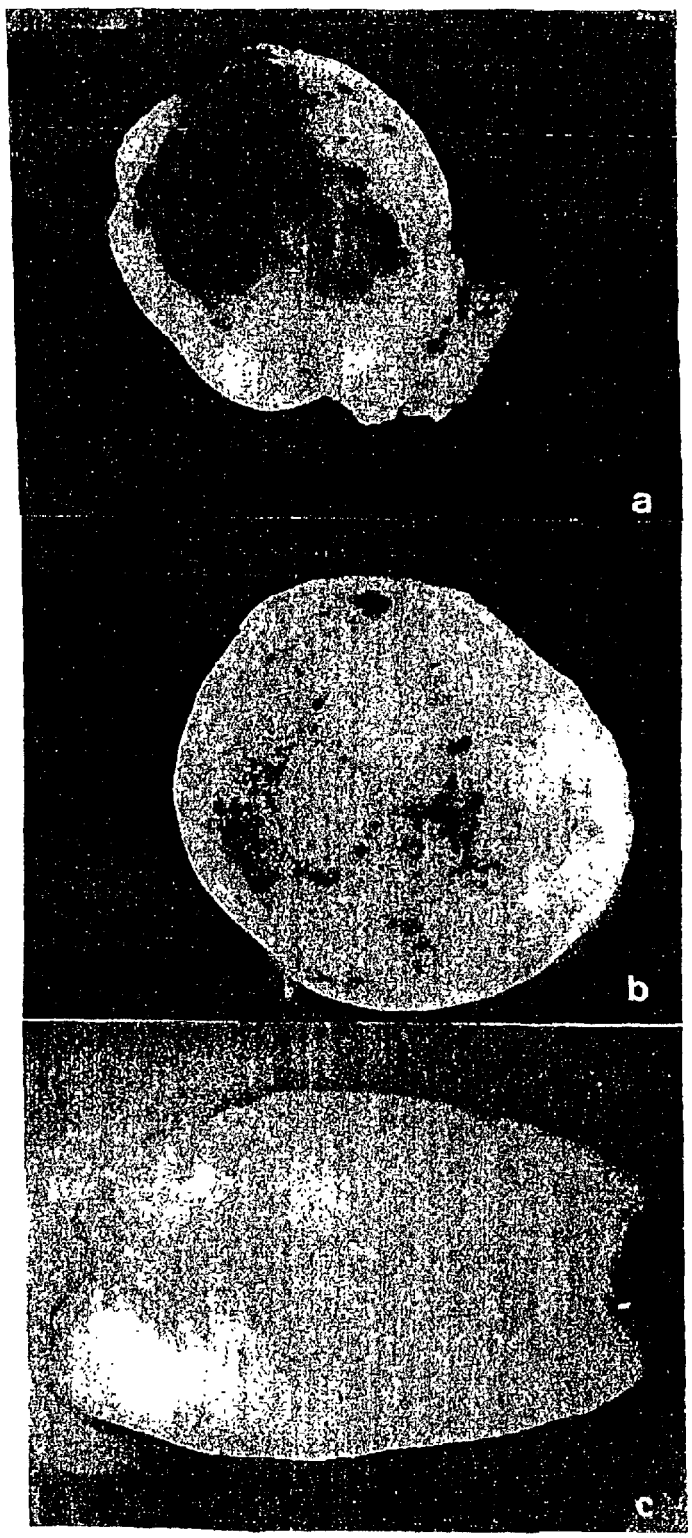
FIG. 7 shows transient expression of LtpW1 regulatory region—GUS (p687LtpW1-GUS) fusion in aleurone of cereal grains delivered by microprojectile bombardment.
Figure 8:
FIG. 8 shows GUS expression in aleurone layer (arrowed) of 3 days germinated kernel of *Z. mays*, T1 self progeny, transformed with p473LtpW1-GUS fusion.
Figure 9:
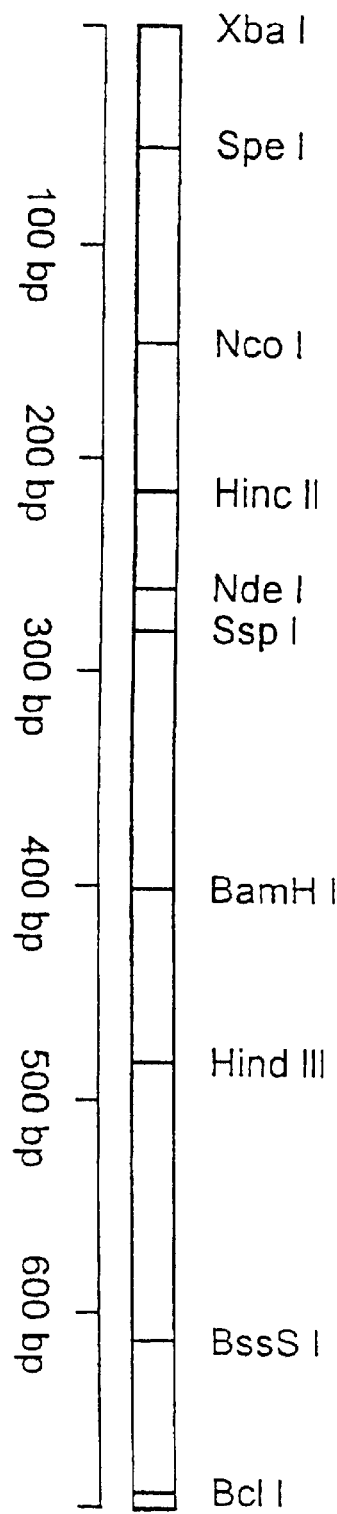
FIG. 9 shows a restriction map of the LtpW1 regulatory region corresponding to the sequence of SEQ ID NO: 1.

LtpW1 exhibits 8.8% of 35S activity and 12.2% activity of the strong rice action monocot constitutive regulatory region (Table 2, Example 3). Comparison of histological evidence of expression of Ltp2 (Kalla et al 1994, Plant J. 6: 849–860)), with FIG. 7 of the present invention (histological evidence of LtpW1 activity) indicates that LtpW1 is more than two times stronger than Ltp2.

Experiments with deletions of the LtpW1 regulatory region indicate that the 473 nucleotide fragment (SEQ ID NO: 2; p473LtpW1) of the full length regulatory region is more active in aleurone tissue than the 687 base pair regulatory region, (SEQ ID NO: 1), p687LtpW1 (Table 3). However, neither the full length regulatory region, nor the 473 bp truncated regulatory region were active in leaf tissue (see Table 4). A truncated regulatory region comprising a 206 bp nucleotide fragment (SEQ ID NO:3, p206LtpW1, also referred to as TAP) of the full length regulatory region was active in aleurone, leaf, and scutellum tissue, functioning as a minimal regulatory region element. This 206 bp region therefore represents a novel, constitutive, regulatory region useful for expressing a gene of interest within plants.

The 206 bp region was also found to direct the expression of a gene of interest within leaf tissue of a range of dicotyledonous plants, including *Soya, Brassica* and *Nicotiana* (Table 6, Example 6). Chimeric constructs comprising the strong monocot promoter, the rice actin promoter (McElroy D., Zhang, W., Cao, J., and Wu, R. 1990. Plant Cell 2: 163–171) were also introduced into these plants, and no activity was observed. These results indicate that the 206 bp region also represents a novel constitutive regulatory region active in a range of plants, including both dicotyledonous and monocotyledonous plants. Deletion and mutational analysis, and other modifications of the TAP regulatory element, including the preparation of chimeric regulatory elements, indicate that the level of TAP activity can be increased in both monocot and dicot plants (example 7).

FIG. 3 shows the sequence of the LtpW1 gene comprising the regulatory element region as identified in SEQ ID NO: 1. The numbering of the regulatory region in FIG. 3 is from base pairs −687 to −1, while the coding region of the gene is from base pairs +1 to 753. Therefore, p687LtpW1 comprises the sequence of SEQ ID NO:1 (nucleotides 1–687), which are equivalent to the sequence of base pairs −687 to −1 of FIG. 3. p473LtpW1 comprises the sequence of SEQ ID NO:2, nucleotides 214–687 of SEQ ID NO: 1, or bps −473 to −1 of FIG. 3. p206LtpW1 comprises the sequence of SEQ ID NO:3, nucleotides 481–687 of SEQ ID NO:1, or bps −206 to −1 of FIG. 3.

By "regulatory element" or "regulatory region", it is meant a portion of nucleic acid typically, but not always, upstream of a gene, and may be comprised of either DNA or RNA, or both DNA and RNA. The regulatory elements of the present invention includes those which are capable of mediating organ specificity, or controlling developmental or temporal gene activation. Furthermore, "regulatory element" includes promoter elements, core promoter elements, elements that are inducible in response to an external stimulus, elements that are activated constitutively, or elements that decrease or increase promoter activity such as negative regulatory elements or transcriptional enhancers, respectively. It is also to be understood that enhancer elements may be repeated thereby further increasing the enhancing effect of an enhancer element on a regulatory region. In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as listed above) that modify gene expression. It is to be understood that nucleotide sequences, located within introns, or 3' of the coding region sequence may also contribute to the regulation of expression of a coding region of interest. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or fragments thereof, of the present invention may be operatively associated with heterologous or exogenous regulatory elements or promoters in order to modulate or mediate the activity of the heterologous regulatory element. Such modulation includes enhancing or repressing transcriptional activity of the heterologous regulatory element, modulating post-transcriptional events, or both enhancing or repressing transcriptional activity of the heterologous regulatory element and modulating post-transcriptional events. For example, one or more regulatory elements, or fragments thereof, of the present invention may be operatively associated with enhancer or silencer elements, to mediate the activity of such regulatory elements within a variety of plants. Furthermore, an intron, for example, but not limited to, the IVS6 intron from maize (Callis, J., 1987, Genes Dev. 1: 1183–1200), or the maize actin intron (McElroy, D. et al., 1991. Mol. Gen. Genet. 231: 150–160), may be included for optimizing expression within monocotyledonous or dicotyledonous plants.

An "analogue" of the regulatory elements described herein include any substitution, deletion, or additions to the sequence of a regulatory element provided that the analogue maintains at least one regulatory property associated with the activity of the regulatory element. Such regulatory properties include directing expression of a gene in operative association with the regulatory element in one or more tissues, or directing organ-specific expression, imparting tissue specificity, or a combination thereof, or temporal activity, or developmental activity, or a combination thereof, or other regulatory attributes including, constitutive activity, negative regulatory elements, enhancer sequences, or sequences that affect stability of the transcription or translation complexes or stability of the transcript.

The DNA sequences of the present invention thus include the DNA sequences of SEQ ID NO: 1 to 11, and 22 to 26, the regulatory regions and fragments thereof, as well as analogues of, or nucleic acid sequences comprising about 80% similarity with the nucleic acids as defined in SEQ ID NO's: 1 to 11 or 22 to 26. Analogues (as defined above), include those DNA sequences which hybridize under stringent hybridization conditions (see Maniatis er al., in Molecular Cloning, (A Laboratory Manual), Cold Spring Harbor Laboratory, 1982, p. 387–389) to any one of the DNA sequence of SEQ ID NO: 1 to 11 and 22 to 26, provided that said sequences maintain at least one regulatory property of the activity of the regulatory element as defined herein.

An example of one such stringent hybridization conditions may be hybridization in 4×SSC at 65° C., followed by washing in 0.1×SSC at 65° C. for an hour. Alternatively an exemplary stringent hybridization condition could be in 50% formamide, 5×SSC at 42° C. and washing in from about 0.5×SSC to about 0.2×SSC at 65° C., Analogues include those DNA sequences which hybridize to any one of the sequences of SEQ ID NO: 1 to 11 and 22 to 26 under these hybridization conditions.

A constitutive regulatory element directs the expression of a gene throughout the various parts of a plant and continuously throughout plant development. Examples of known constitutive regulatory elements include promoters associated with the CaMV 35 S transcript. (Odell et al., 1985, *Nature*, 313: 810–812), the rice actin 1 (Zhang et al, 1991, *Plant Cell*, 3: 1155–1165) and triosephosphate isomerase 1 (Xu et al, 1994, *Plant Physiol.* 106: 459–467) genes, the maize ubiquitin 1 gene (Cornejo et al, 1993, *Plant Mol. Biol.* 29: 637–646), the *Arabidopsis* ubiquitin 1 and 6 genes (Holtorf et al, 1995, *Plant Mol. Biol.* 29: 637–646), T1275 (U.S. Pat. No. 5,824,872), and the tobacco translational initiation factor 4A gene (Mandel et al, 1995 *Plant Mol.*

Biol. 29: 995–1004). The regulatory element, p206LtpW1, as described herein, is another example of a constitutive regulatory element.

The present invention also includes a chimeric regulatory region comprising the p206Ltp (also referred to as TAP) regulatory region as defined by SEQ ID NO:3, or a nucleic acid that hybridizes to SEQ ID NO: 3, as defined above, a fragment of p206Ltp (TAP) regulatory region, for example but not limited to, fragments as defined by SEQ ID NO's: 5 to 11, or a substituted, modified, or mutated regulatory region, for example but not limited to the regulatory regions defined in SEQ ID NO's 22–26, and one or mediators of this regulatory activity. By "mediate", it is meant the activity associated with an exogenous regulatory element that further regulates the activity of p206Ltp. For example, which is not to be considered limiting in any manner, a mediator may either up regulate, down regulate the activity of TAP, and comprise one or more enhancer or silencer elements, respectively. Examples of enhancer elements are known in the art, and include, but are not limited to, enhancers active in dicotyledonous and monocotyledonous plants, the 35 S enhancer, actin enhancer, and the enhancer from T1275 (BstI element; U.S. Pat. No. 5,824,872, which is incorporated herein by reference). Furthermore, chimeric regulatory elements comprising p206Ltp or an analogue or fragment thereof may also include, but are no limited to, the addition of one or more GCC boxes, one or more G boxes or other sequences that may otherwise regulate the regulatory region activity of the regulatory region (see for example FIG. 13(B)). Regulatory region activity associated with such chimeric regulatory regions have been demonstrated in monocots (FIG. 14(A)) and dicots (FIG. 14(C)). However, it is to be understood that other chimeric TAP regulatory regions may also be prepared that exhibit desirable regulatory region properties including increasing, or modulating regulatory activity.

Nucleic acid constructs comprising a chimeric regulatory region associated with 206LtpW1 were therefore examined to determine if exogenous regulatory regions, mediators, may further regulate the activity of TAP. Transient expression assays indicate that a dicot enhancer element, for example but not limited to an enhancer obtained from tobacco, is active in increasing the activity of 206LtpW1 in plants (e.g. Table 6, Example 6). Similarly, one or more GCC boxes or one or more G boxes are also able to enhance TAP activity (see FIGS. 14(A) and 14(C)) in both monocot and dicot plants. Therefore, the present invention is also directed to gene constructs comprising a chimeric 206LtpW1 regulatory region, comprising p206 or a fragment or analogue thereof in association with at least one other exogenous regulatory region. The present invention also pertains to the use of a chimeric regulatory region as just described in operative association with a gene of interest.

Any exogenous gene, or gene of interest, can be used and manipulated according to the present invention to result in the expression of the exogenous gene.

By "gene of interest" it is meant any gene that is to be expressed within a host organism. Such a gene of interest may include, but is not limited to, a gene that encodes a protein directed at improving an agronomic trait of the plant, for example but not limited to improving plant defence against pathogens, or resistance to herbicides. A gene of interest may also include, but is not limited to, a gene that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-α, interferon-β, interferon-τ, blood clotting factors, for example, Factor VIII, Factor IX, or tPA or combinations thereof. A gene of interest may also encode an industrial enzyme, protein supplement, nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis etc.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium rumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene. The 3' untranslated region from the structural gene of the present construct can therefore be used to construct chimeric genes for expression in plants.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

The data presented herein indicate that nucleotides 1–214 and 215–481 of SEQ ID NO: 1 are responsible for imparting tissue specificity within this regulatory region, since once the nucleotides 1–481 are removed from the full length regulatory region, tissue specificity is lost (Table 4). It is contemplated that either of these regions may be combined with any suitable regulatory region of interest, for example, which is not to be considered limiting, a minimal, constitutive, or viral promoter etc. in order to obtain aleurone-specific expression of a gene linked thereto. Both of these regions were found to comprise very low sequence similarity with other sequences present within gene sequence databases such as GenBank.

Furthermore, the data presented in Table 3 indicates that the region comprising nucleotides 1–481 of SEQ ID NO: 1 is responsible for regulating the strength of regulatory region activity, and includes both silencer- and enhancer-type activities. For example, the fragment comprising nucleotides 215–481 of SEQ ID NO:1 may be used as an enhancer like element as constructs comprising this region (e.g. p473LtpW1) resulted in increased expression when compared with either the full length regulatory region (p687LtpW1) or the truncated regulatory region p206LtpW1 (see Table 3). Similarly, nucleotides 482–687 (of SEQ ID NO:1) also exhibit enhancer-type activity, since constructs comprising this region (p206LtpW1) exhibited higher levels of expression than the full length regulatory region. Therefore, it is contemplated that nucleotides 214–481, or 482–687 of SEQ ID NO: 1 may be combined with any suitable regulatory region of interest, for example, which is not to be considered limiting, a minimal, constitutive, or viral promoter etc., in order to obtain both aleurone-specific expression of a gene linked thereto, as well as increased gene expression.

The present invention also pertains to the p687LtpW1 regulatory region comprising additional enhancer or silencer elements, or further comprising modifications to the sequence of these regulatory regions, for example mutations, additions or substitutions as described in, but not limited to those of FIG. 13(A), or (B).

Similarly, the fragment comprising nucleotides 1–214 comprises silencer-type elements as constructs comprising this region (e.g. p687LtpW1) result in lower levels of expression compared with the levels of expression obtained with either of the truncated regulatory region constructs, p206LtpW1, or p473LtpW1 (see Table 3). It is contemplated that nucleotides 1–214 may be combined with any suitable regulatory region of interest, for example, which is not to be considered limiting, a minimal, constitutive, or viral promoter etc., in order to obtain both aleurone-specific expression of a gene linked thereto, along with reduced gene expression.

The truncated regulatory region, p473LtpW1, was used to transform maize, where it was noted that this regulatory region was active only in aleurone of developing and germinating cereal grain.

In transient assays, activity of the 206 bp HinII/BclI truncated regulatory element (SEQ ID NO₃; FIG. 3) in non-aleurone tissues was relatively low (7–11%) compared to other constitutive promoters (see Table 4, Example 3). However, the level of stable expression in transformed plants (FIG. 10) was high, equalling the activity observed for the expression of a gene of interest under the control of a strong monocot regulatory element, the rice actin promoter (McElroy D., Zhang, W., Cao, J., and Wu, R. 1990. Plant Cell 2: 163–171). Chimeric TAP regulatory regions were also found to be active in directing the expression of a gene of interest in monocot and dicot tissues (see FIGS. 14(A) and (C)). Therefore, it is contemplated that the p206 (TAP) region may also be combined with any suitable regulatory region of interest, for example, which is not to be considered limiting, a minimal, constitutive, or viral promoter etc. in order to obtain aleurone-specific expression of a gene linked thereto.

Figure 12A:
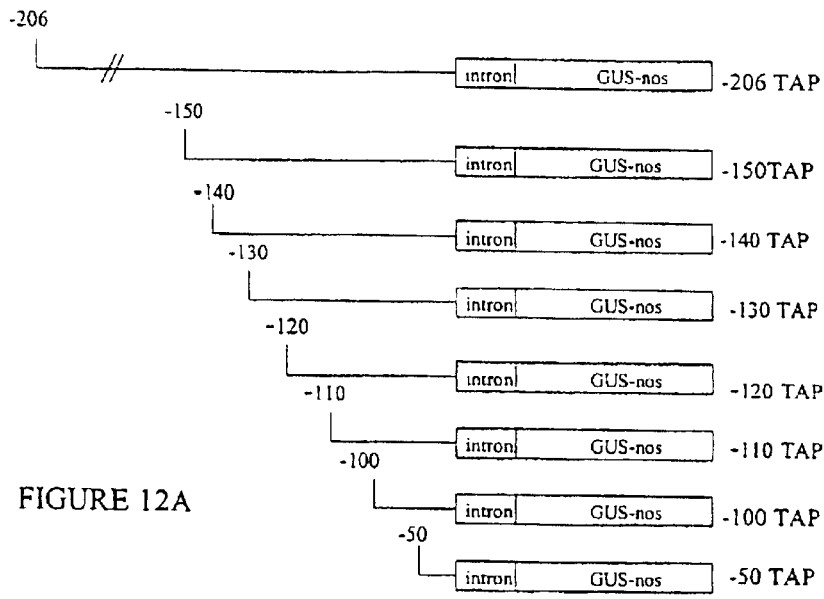
FIG. 12(A) shows a diagrammatic representation of the 5' deletion series of the TAP regulatory region fused to the reporter GUS.

Deletion analysis of the TAP regulatory region (constructs outlined in FIG. 12(A)) indicate that from −206 to about −110 (nucleotides 1–98 of SEQ ID NO:3) of the TAP regulatory region did not have any appreciable effect of the activity of the p206Ltp regulatory region in monocots, for example corn. However, the region between −100 and −110 (nucleotides 90 to 108 of SEQ ID NO:3) was observed to be required for high expression levels.

Figure 14A:
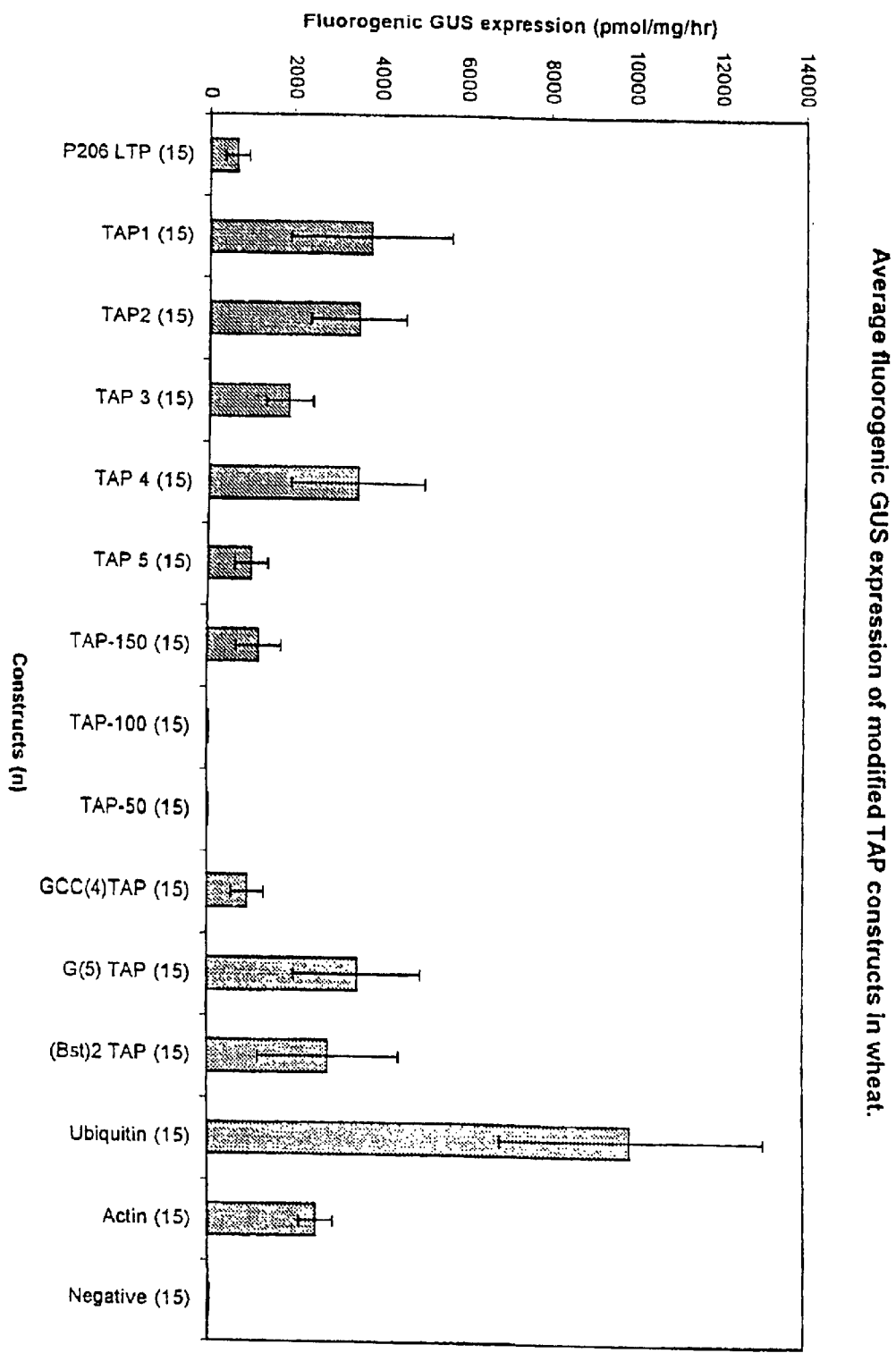
FIG. 14(A) shows the activity of a mutational series TAP 1 to TAP 5, and several deletion constructs, TAP-150, TAP-100, and TAP-50, and several chimeric regulatory regions, GCC(4)TAP, G(5)TAP, (Bst)2TAP in wheat callus.
Figure 14B:
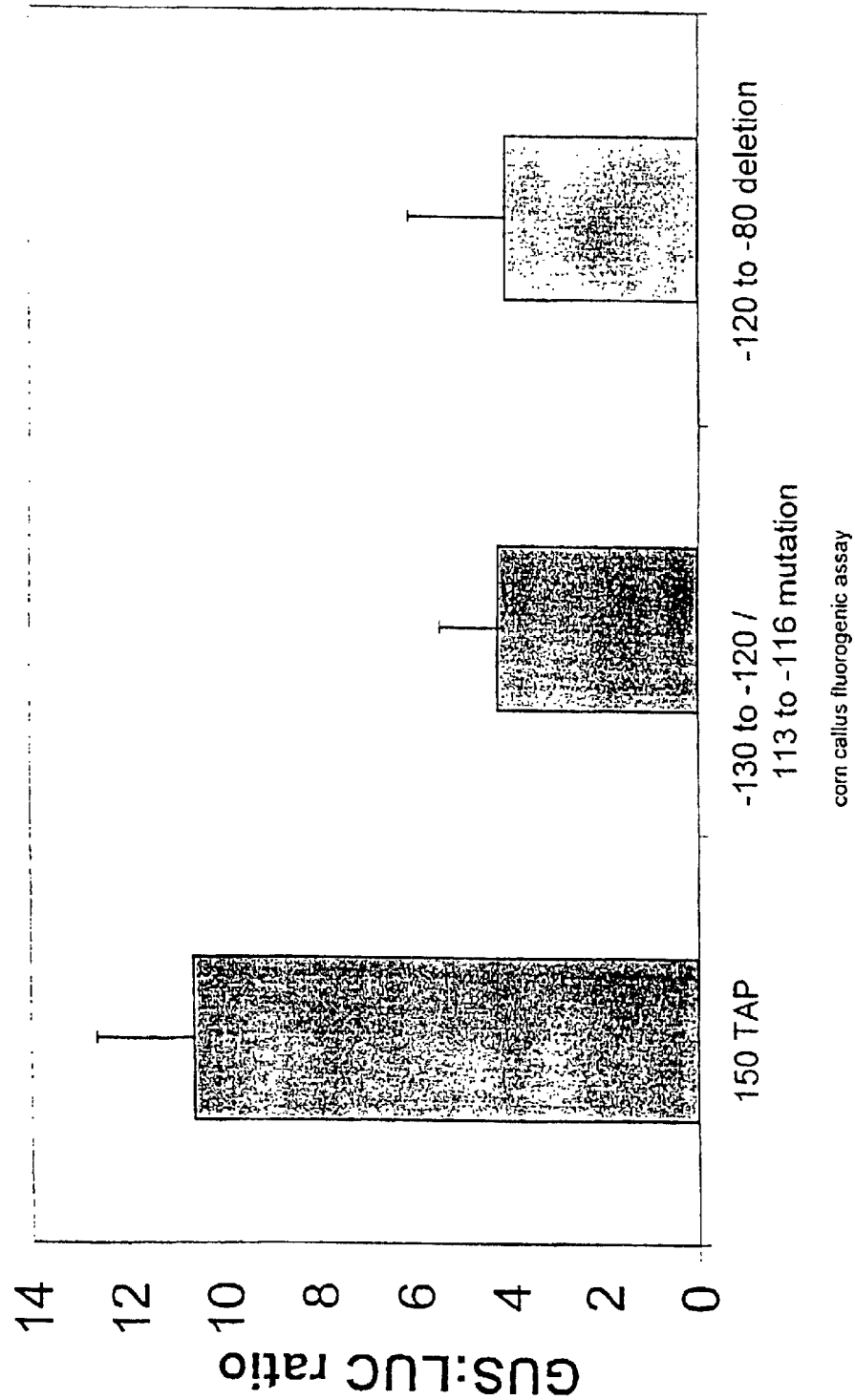
FIG. 14(B) shows the activity of three other modified TAP regulatory regions within wheat callus.
Figure 14C:
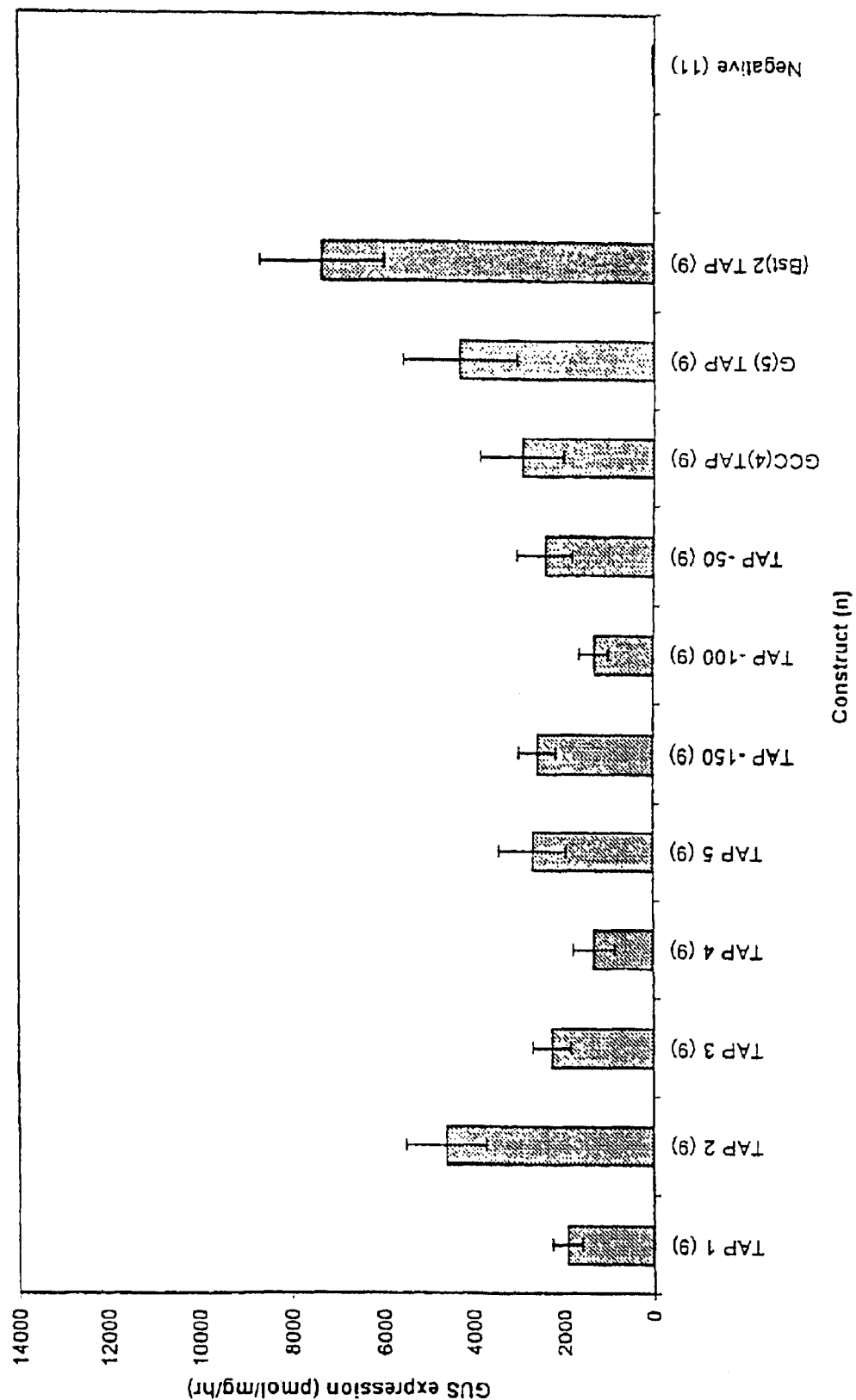
FIG. 14(C) shows the activity of a mutational series TAP 1 to TAP 5, and several deletion constructs, TAP-150, TAP-100, and TAP-50, and several chimeric regulatory regions, GCC(4)TAP, G(5)TAP, (Bst)2TAP in tobacco leaf cells.

The −150 TAP (regulatory region defined in SEQ ID NO: 5), −100 TAP (regulatory region defined in SEQ ID NO:10) and −50 TAP (regulatory region defined in SEQ ID NO: 11) regulatory region in monocots is shown in FIG. 14(A), and in dicots is shown in FIG. 14(C). In monocots, high levels of regulatory region activity are observed with the −150 TAP construct (FIG. 14(B)), while the removal of the −150 region removed any activity, as indicated with the activity associated with the −100 TAP construct compared with the −150 TAP construct (FIG. 14(A)), or the −120 to −80 region (regulatory region defined in SEQ ID NO: 12; FIG. 14(B)). These results suggest that one or more core regulatory elements reside within this region (i.e. the −150 to −100- region; nucleotides 58 to 108 of SEQ ID NO:3).

Nucleotides 89–96 of SEQ ID NO:3 are AT rich. To determine if this region is involved with the activity of the TAP regulatory element, a construct was prepared comprising substitutions in this region (−130 to −120/−113 to −116 mutation construct, having a regulatory region defined in SEQ ID NO:13). This construct resulted in a decrease in activity in monocots (FIG. 14(B)).

Analysis of the deletion constructs in dicots indicates that significant activity is associated with the −150 TAP, −100 TAP and the −50 TAP constructs (regulatory regions defined in SEQ ID NO's: 5, 10 and 11, respectively). Since there is no loss of activity with the removal of the −150 to −100, or −50 region, as was observed in monocots, this demonstrates that the sequence from −50 to −1 (nucleotides 158 to 206 of SEQ ID NO:3), exhibits regulatory region activity in dicots.

Several alterations and substitutions of the TAP regulatory region were also examined for regulatory region activity. Example of constructs TAP1 to TAP 5, which are not to be considered limiting in any manner, are shown in FIG. 13(A) (regulatory regions defined in SEQ ID NO's: 22–26). The TAP 1 to TAP 4 constructs all exhibit a large increase in activity in monocots when compared with the activity associated with the p206Ltp (TAP) construct. These data demonstrate that the regulatory region activity may be enhanced through the mutation, alteration, or substitution of nucleotides within the TAP sequence. It is also to be understood that the modifications described above to the TAP regulatory region, as well as chimeric regulatory region constructs, may also be included within the full length Ltp regulatory region, including the p687LtpW1 or p473LtpW1 regulatory regions, or fragments thereof.

Analysis of the mutation constructs disclosed in FIGS. 13(A) and (B) were also examined in dicots as shown in FIG. 14(C). The TAP 1 to TAP 5 constructs all exhibit a similar level, or an increase in the level of regulatory region activity when compared with the activity associated with the p206Ltp (TAP) construct. Chimeric regulatory elements comprising (Bst)₂ TAP, GCC (4) TAP or G(5) TAP exhibit an increase in regulatory region activity (FIG. 14(C)).

Collectively these results demonstrate that substitutions or additions to the Ltp regulatory region, preferably the p206Ltp region, are functional in both monocot and dicot plants, and result in increased activity in both monocot and dicot plants.

The gene constructs of the present invention can also include other optional regulatory motifs such as enhancers, either translation or transcription enhancers, as may be required. These enhancer regions are well known to persons skilled in the art, and can include, for example, the enhancer region of the 35S regulatory region, as well as other enhancers obtained from other regulatory regions, and/or the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

Also considered pan of this invention are transgenic plants containing the chimeric gene construct of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, embryo or shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421–463 (1988); Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebrve, D E Layzell (eds), Addison Wesly, Langmans Ltd. London, pp. 561–579 (1997). The present invention further includes a suitable vector comprising the chimeric gene construct.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLE 1

Localization of Ltp1 Expression

Figure 1:
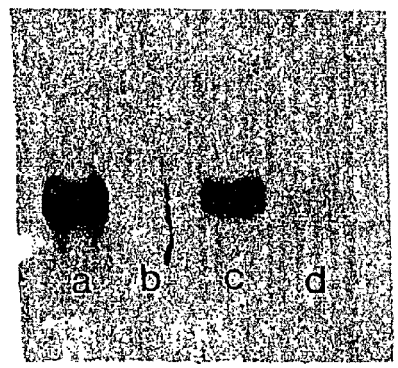
FIG. 1 shows Ltp expression in aleurone tissues of *Hordeum* and *Triticum* species using Northern analysis hybridized with a barley Ltp1 DIG-labelled cDNA.

In order to isolate genes which are functional in aleurone of developing and germinating wheat grain, a barley cDNA probe of an aleurone specific lipid transfer protein gene (Ltp1,) was used to indicate activity of similar genes in wheat aleurones during seed development. Northern blot analyses using a DIG-labelled barley cDNA probe showed that Ltp transcripts were present in aleurone tissue 20 dpa (FIGS. 1(*a*) and 1(*c*)). No activity was detected in early wheat grain development, 10 dpa (FIG. 1(*b*) but could be detected in *T. turgidum* (FIG. 1(*d*)).

Figure 2:
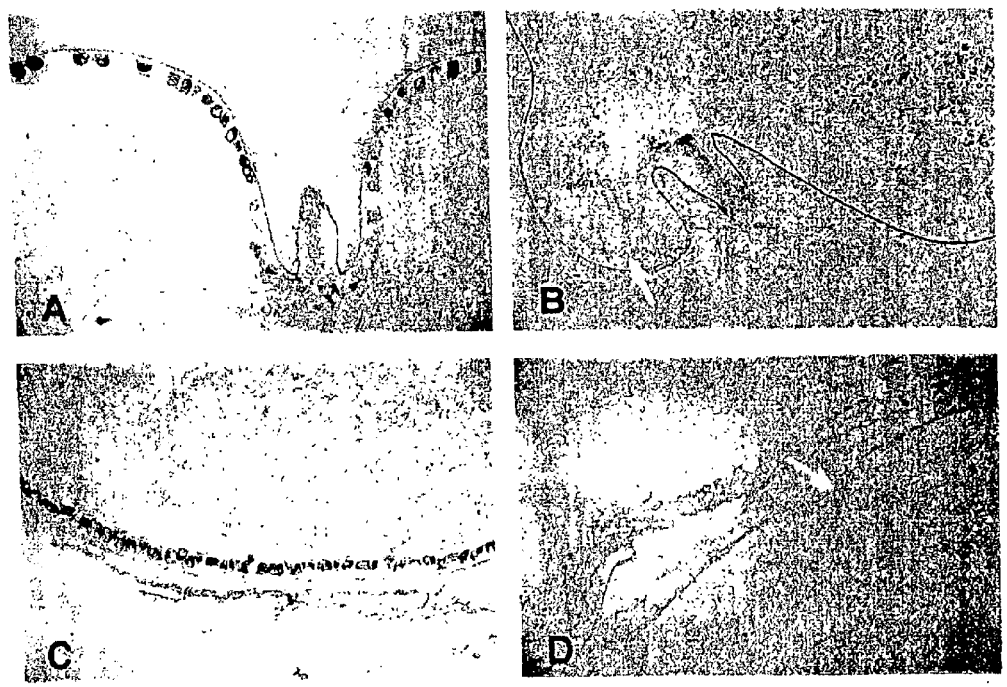
FIG. 2 shows RNA in situ hybridization of $^{35}$S-labelled barley Ltp ribo-probe in 73h germinating, and 18 dpa developing wheat grain.

In situ hybridization (based on a modification of the procedure outlined in Cox and Goldberg, 1998, Analysis of Plant Gene Expression, In Plant Molecular Biology. A Practical Approach, pp. 1–34) performed on cross sections of developing and germinating grain showed that Ltp expression was limited to aleurone cells. A $^{35}$S Ltp antisense ribo-probe hybridized strongly to aleurone cells (FIG. 2(*a*)), whereas no differential hybridization was observed with the sense RNA probe (FIG. 2(*b*)). Ltp expression was observed throughout grain development after 18 dpa and during germination up to 73 h post-imbibition at which time the endosperm was depleted. No hybridization was observed in developing endosperm, embryo or pericarp tissues (data not shown).

EXAMPLE 2

Genomic DNA of LtpW1

Genomic DNA was isolated from young leaf tissue of hexaploid wheat, (*T. aestivum*) and digested with XbaI. When this DNA was analysed by Southern blot using standard procedures and a DIG-labelled barley Ltp cDNA probe, three loci for the Ltp1 gene (at 1.5, 6.0, and 7.0 kb) were detected. The copy corresponding to the 1.5 kb XbaI band was cloned by screening a λ long C phage library of size-restricted XbaI fragments with a barley Ltp1 cDNA probe.

LtpW1 refers to the Ltp gene contained within the 1.5 kb XbaI digested *T. aestivum* genomic clone, the sequence of which is shown in SEQ ID NO: 4 (also see FIG. 3).

The coding sequence of LtpW1 shares 85% DNA identity with the barley Ltp1 (FIG. 4(*a*)), includes a 26 amino acid transit peptide for cell wall localization of the protein, and has one predicted 88 bp intron which is 44 bp shorter than the equivalent barley intron. The nucleotide sequences LtpW1 and barley Ltp 1 promoter (Linnestad 1991) are well conserved for approximately 140 bp upstream of the ATG start codon whereupon they diverge considerably (FIG. 4(*a*)). The conserved promoter region includes the putative cap and TATA sites but not the proposed CAT site or other regulatory elements (see FIGS. 3, and 4(*a*)).

The nucleotide sequence of the LtpW1 regulatory region exhibits little or no identity with the barley Ltp2 promoter (FIG. 4(*b*)). The LtpW1 regulatory region was shown to be active in aleurone of developing and germinating cereal grain which is uniquely different from the barley Ltp2 promoter which is only active during grain development but not during germination (Kalla et al 1994).

EXAMPLE 3

Expression of GUS Under the Control of LtpW1 Aleurone Regulatory Regions p687LtpW1-GUS A 687 bp XbaI/BcII regulatory region fragment (SEQ ID NO: 1; FIG. 3) was subcloned from pLtpW1 and fused to a GUS promoterless reporter cassette (pLC-GUS). pLC-GUS was obtained by removing the 35S promoter as a SacI fragment from pZO1016 (designated p35S-GUS herein), which was a gift from R. Sinibaldi, Sandoz, Ca. A 687 bp XbaI/BcII fragment was isolated from pTALP1 (containing the 1.5 kb XbaI-digested *T. aestivum* genomic clone) and the sticky ends were filled-in with Klenow fragment of DNA polymerase. This fragment was blunt-end ligated into the SmaI site of pLCGUS (see FIG. 5(*d*)), and the orientation of the insert was checked by digesting with BamHI. The activity of this regulatory region was compared with that of the promoterless construct (pLC-GUS) as well as to constructs comprising constitutive CaMV35S and rice action promoters (see FIGS. 6(a) and (b), respectively). These constructs were used for comparison of promoter activities. The 35S promoter is described in: Odel, J. T., Nagy, F. and Chua N-H (1985) Nature 313: 810–812. The rice actin promoter is described in: McElroy D., Zhang, W. Cao, J. and Wu, R. (1990) Plant Cell 2: 163–171.

These constructs were introduced into the aleurone of cereal grains by microparticle bombardment using standard methods. LUC and GUS constructs ware co-bombarded in equimolar amounts and GUS is expressed relative to LUC to minimize variability between reps (shots). LUC activity serves as an internal control for the shot to shot variability.

Tissues, 48 h post-bombardment, were incubated in reaction buffer containing 50 mM $NaH_2PO_4$ (pH 7.0), 10 mM EDTA and 1 mM 5-bromo-4-chloro-3-indolyl-B-glucoronide (X-Gluc), 0.5 mM$MK_3[Fe(CN)_6]$, 0.5 mM$K_4$ $[Fe(CN)_6]$ at 37° C. for 4–20 h. A blue precipitate in the bombarded cells indicates activity of B-glucuronidase. The regulatory region gave high expression of GUS in histological transient assays with wheat aleurones (FIG. 7(a)). Activity was also demonstrated in maize and barley aleurones (FIGS. 7(b) and (c)) The 687 bp regulatory region fragment showed no activity in leaf, root or coleoptile tissues of wheat (data not shown).

In quantitative expression assays in wheat aleurone the 687 bp regulatory region had 3.4% of the activity of the constitutive 35S promoter (Table 1). This underestimates the relative aleurone-directed activity of the LtpW1 regulatory region because of additional endosperm-derived activity of the constitutive 35S promoter.

TABLE 1

Activity of p687LtpW1 in 12 dpa wheat aleurone

| Construct | Luciferase (mv/sec/mg protein) | GUS (pmol MU/min/mg protein) | GUS/LUC | %35S Activity |
|---|---|---|---|---|
| Au | 2001 | 0 | 0 | — |
| pLC-GUS[2]/p35S-LUC | 2100 | 0 | 0 | — |
| p35S-GUS/p35S-LUC | 3400 | 30072 | 8.84 | — |
| p687LtpW1-GUS/ p35S-LUC | 4200 | 1247 | 0.3 | 3.4 |

[1]mean of three sets of bombardments
[2]promoterless construct

P473LtpW1-GUS

A truncated version of the LtpW1 regulatory region (see SEQ ID NO:2; nucleotides 473 to −1 of FIG. 3; or nucleotides 214–87 of SEQ ID NO:1) was prepared by digesting pTALTP1 with HincII and BclI, and the resulting 0.47 kb fragment (after treatment with Klenow) was ligated into the SmaI site of pLC-GUS. Orientation of the insert was checked by digesting the resulting recombinant plasmid with BamHI. The construct (p473LtpW1-GUS) thus obtained showed 8.8% and 12.2% activity of the constitutive 35S and rice action promoters, respectively (pAct-GUS was a gift from Ray Wu at Cornell). See Table 2 for results.

TABLE 2

Activity of p473LtpW1 in 12 dpa wheat aleurone

| Construct | Luciferase (mv/sec/mg protein) | GUS (pmol MU/min/mg protein) | GUS/LUC | %35S Action Activity |
|---|---|---|---|---|
| Au | 2001 | 0 | 0 | — |
| pLC-GUS[2]/p35S-LUC | 1300 | 0 | 0 | — |
| p35S-GUS/p35S-LUC | 3500 | 8077 | 2.31 | — |
| pAct-GUS/p35S-LUC | 3300 | 5524 | 1.67 | |
| p473LtpW1-GUS/ p35S-LUC | 3200 | 651 | 0.2 | 8.8 12.2 |

[1]mean of three sets of bombardments
[2]promoterless construct

When compared within a single experiment, the 473 bp fragment was 170% as active as the 687 bp fragment (Table 3).

TABLE 3

Activity of p687LtpW1, p473LtpW1, and p206LtpW1 in 7 dpa wheat aleurone

| Construct | Luciferase (mv/sec/ mg/protein) | GUS (pmol MU/min/mg protein) | GUS/LUC | %35S Activity |
|---|---|---|---|---|
| pLC-GUS[2]/p35S-LUC | 97001 | 120 | 0.01 | 0.1 |
| p35S-GUS/p35S-LUC | 2300 | 18305 | 7.96 | — |
| p206LtpW1-GUS/ p35S-LUC | 7900 | 1781 | 0.23 | 2.9 |
| p473LtpW1-GUS/ p35S-LUC | 6800 | 2399 | 0.35 | 4.4 |
| p687LtpW1-GUS/ p35S-LUC | 5100 | 1090 | 0.21 | 2.6 |

[1]mean of three sets of bombardments
[2]promoterless construct

P206LtpW1-GUS

To generate p206LtpW1-GUS, pTALTP1 was digested with BclII, then with HindIII, and the 0.2 kb fragment was isolated from a gel and purified. The sticky ends were filled in with Klenow and the resulting fragment was ligated into the SmaI site of pLC-GUS. Neither the 687 bp or 473 bp regulatory regions was active in leaf tissue but the 206 bp HinII/BclI truncated regulatory region (SEQ ID NO:3; nucleotides −206 to −1 of FIG. 3; nucleotides 481–687 of SEQ ID NO:1) had 7.5% the activity of the 35S promoter in leaf (Table 4).

TABLE 4

Activity of p687LtpW1, p473LtpW1, and p206LtpW1 in wheat leaf tissue

| Construct | Luciferase (v/sec/mg/ protein) | GUS (pmol MU/min/mg protein) | GUS/LUC | %35S Activity |
|---|---|---|---|---|
| pLC-GUS[2]/p35S-LUC | 2001 | 1.6 | 0.007 | 0.7 |
| p35S-GUS/p35S-LUC | 200 | 204.3 | 1.02 | — |
| p206LtpW1-GUS/ p35S-LUC | 200 | 15.3 | 0.077 | 7.5 |
| p473LtpW1-GUS/ p35S-LUC | 700 | 1.3 | 0.002 | 0.2 |
| p687LtpW1-GUS/ p35S-LUC | 700 | 1.7 | 0.002 | 0.2 |

[1]mean of three sets of bombardments
[2]promoterless construct

Similarly, in wheat scutellum tissue, only the 206 bp regulatory region fragment was active (Table 5) with activities of 11.4% of 35S and 8.5% of rice actin promoters.

TABLE 5

Activity of p687LtpW1, p473LtpW1, and p206LtpW1 in 20 dpa wheat scutellum tissue

| Construct | Luciferase (v/sec/mg/ protein) | GUS (pmol MU/min/mg protein) | GUS/LUC | %35S Action Activity |
|---|---|---|---|---|
| pLC-GUS[2]/p35S-LUC | 13001 | 37 | 0.028 | 0.23,0.17 |
| p35S-GUS/p35S-LUC | 400 | 4873 | 12.182 | — |
| pAct-GUS/p35S-LUC | 400 | 6530 | 16.325 | — |
| p206LtpW1-GUS/p35S-LUC | 100 | 139 | 1.39 | 11.41, 8.51 |
| p473LtpW1-GUS/p35S-LUC | 200 | 2 | 0.01 | 0.08, 0.06 |
| p687LtpW1-GUS/p35S-LUC | 200 | 6 | 0.03 | 0.24, 0.18 |

[1]mean of three sets of bombardments
[2]promoterless construct

Thus the nucleotide sequence between 206 bp and 473 bp determines the tissue and stage dependent regulation of the LtpW1 regulatory region.

Collectively, these data indicate that:

i) nucleotides 1–214 and 215–481 of SEQ ID NO:1 are responsible for imparting tissue specificity within this regulatory region. Removal of either of these regions from the full length regulatory region results in greatly reduced tissue specificity (Table 4).

ii) the region comprising nucleotides 1481 of SEQ ID NO: 1 is responsible for regulating the strength of regulatory region activity, and includes both silencer- and enhancer-type activities:

iii) the fragment comprising nucleotides 214481 of SEQ ID NO: 1 exhibits enhancer-like activity as constructs comprising this region (e.g. p473LtpW1) resulted in increased expression when compared with either the full length regulatory region (p687LtpW1), or the truncated regulatory region p206LtpW1 (see Table 3). Similarly, nucleotides 482–687 also exhibit enhancer-type activity, since constructs comprising this region (p206LtpW1) exhibited higher levels of expression than the full length regulatory region;

iv) the fragment comprising nucleotides 1–214 comprises silencer-type elements as constructs comprising this region (e.g. p687LtpW1) result in lower levels of expression compared with the levels of expression obtained with either of the truncated regulatory region constructs, p206LtpW1, or p473LtpW1 (see Table 3);

v) the 206 bp version of the LtpW1 regulatory region represents a novel, constitutive promoter, for monocotyledonous plants Because of the relatively superior activity of the 473 bp fragment in aleurone tissue (Tables 1, 2 and 3), this version was used for transformation of maize.

EXAMPLE 4

Preparation of Transgenic Plants of *Zea Mays*

To verify that the 5' flanking sequence from the genomic clone LtpW1 contained the regulatory sequences required to confer expression in aleurone cells, the 473 bp LtpW1/GUS fusion was co-bombarded with a bialaphos selectable plasmid (pAHC25) into embryogenic cultures of maize. Transgenic calli were selected on bialaphos media and transgenic plants regenerated. The transgenic plants were screened for GUS activity. The 473 bp LtpW1 regulatory region directed the expression of GUS only in the aleurone layer of developing and germinating transgenic maize kernels (FIG. 6).

EXAMPLE 5

Stable Expression of a Gene of Interest in Monocots Under the Control of p206LptW1 (TAP)

Figure 10:
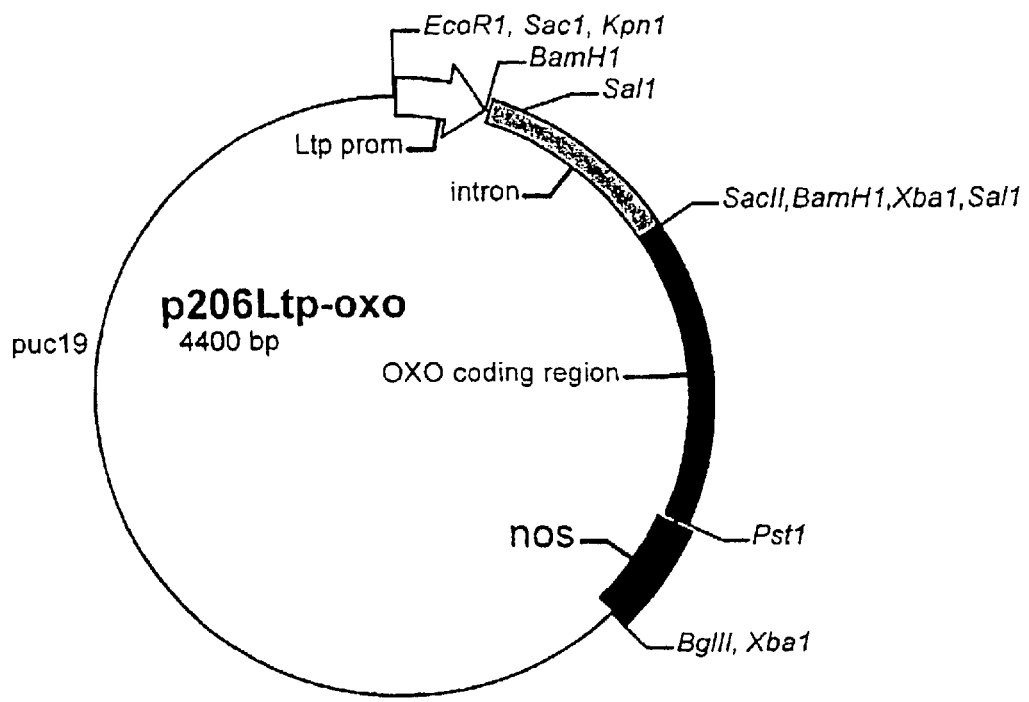
FIG. 10 shows a diagrammatic representation of the p206Ltp-oxo plasmid comprising the 206 fragment of the Ltp regulatory region (Lpt prom), adjoining an intron and the oxo coding region.
Figure 11:
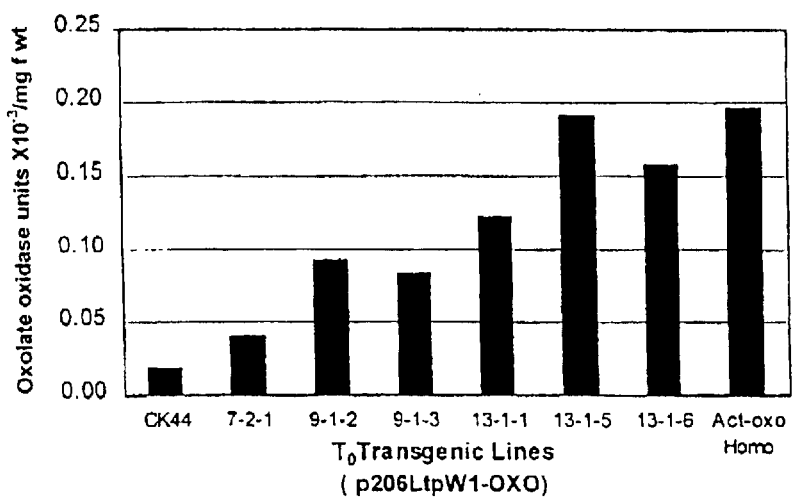
FIG. 11 shows the expression of p206Ltp-oxo in leaf tissue of transgenic corn. CK44 is a non-transformed control, and Act-oxo Homo is an actin-OXO $T_5$ line homozygous for the OXO gene, and is a high expressing positive control. The remaining $T_0$ transgenic lines comprise p206Ltp-oxo.

Several lines of corn were transformed via particle bombardment as described above with a p206Ltp-OXO construct (FIG. 10) which generates oxalate oxidase reporter activity (Byron Lane et al., J. Biol. Chem. 1991, 266: 10461–10469). This construct also contains an intron, for example the IVS6 intron, or the first intron from the actin gene. Plants were also transformed with oxalate oxidase under the control of the strong monocot rice actin promoter (McElroy D., Zhang, W., Cao, J., and Wu, R. 1990. Plant Cell 2: 163–171). Plant tissues were harvested and assayed for oxalate oxidase activity. Plants comprising the oxalate oxidase transgene under the control of p206LtpW1 exhibited substantially higher activity than the non-transformed CK44 line. Line 13-1-5 expressed at 95% of the level obserevd in a line homozygous for the oxalate oxidase transgene, under the control of the rice actin promoter (FIG. 10).

EXAMPLE 6

Activity of p206Lpt (TAP) in Dicotyledons

The activity of the 206 bp HinII/BcII truncated regulatory element (TAP; SEQ ID NO$_3$; FIG. 3) was also examined within dicotyledonous plants to determine whether this regulatory element is active within these plants. Constructs comprising GUS in operative association with TAP (p206LptW1) were prepared as outlined in Example 3, however, an intron (either the IVS6 or actin intron) was included. These constructs were introduced into several dicotyledonous plants using particle bombardment as outlined in Example 3. A chimeric construct comprising TAP (p206LptW1), linked with the BstYI fragment of T1275, an enhancer element obtained from tobacco (see U.S. Pat. No. 5,824,872, which is incorporated herein by reference), and in operative association with GUS, was also examined. The activities of the constructs comprising the p206Lpt (TAP) regulatory region was compared with the activity of the strong monocot rice actin promoter (McElroy D., Zhang, W., Cao, J., and Wu, R. 1990. Plant Cell 2: 163–171). The results are present in Table 6.

TABLE 6

Activity of p-206LtpW1-GUS in leaf tissue of dicotyledonous plants and regulation by an enhancer element, BstY1*

| | Gus Positive Foci per Shot | | |
|---|---|---|---|
| Plasmid | Soya | Brassica | Nicotiana |
| Au* | 1 | 0 | 0 |
| pAct-GUS | 0 | 0 | 6 |

TABLE 6-continued

Activity of p-206LtpW1-GUS in leaf tissue of dicotyledonous plants and regulation by an enhancer element, BstY1*

| | Gus Positive Foci per Shot | | |
|---|---|---|---|
| Plasmid | Soya | Brassica | Nicotiana |
| p206LtpW1-GUS | 3 | 123 | 48 |
| pBstY1-206LtpW1-GUS** | 133 | 91 | 155 |

[1]Mean of three bombardments, assayed 48 hours post-bombardment.
*Au is a gold control, no added DNA.
**BstY1 is the −394 to −62 fragment of T1275 regulatory region (U.S. Pat. No. 5,824,872).

The rice actin monocot expression vector (pAct-GUS) had no activity in Soya and *Brassica* and low activity in *Nicotiana* leaves. However, the 206LtpW1 regulatory region was active in Soya, *Brassica* and *Nicotiana* and exhibited substantially greater activity than the actin promoter in *Brassica* and *Nicotiana*.

These results indicate that the truncated LtpW1 regulatory region, 206LtpW1 (TAP; SEQ ID NO 3) is subject to regulation by chimeric enhancer fragments such as the BstYI element of T1275 (U.S. Pat. No. 5,824,872). The 206LtpW1 regulatory region with the BstYI enhancer element had uniformly high activity in the dicotyledonous plants investigated.

Collectively these results indicate that the truncated regulatory region, p206Ltp, is active in a range of monocot and dicot plants, and its regulatory activity may be modulated in the presence of other exogenous regulatory elements.

EXAMPLE 7

Deletion and mutational analysis of p206Lpt (TAP)
Preparation of Constructs

A series of deletions, mutations, substitutions and additions within the TAP regulatory region were prepared to further characterized this region and its activity within both dicots and monocots.

1) Tap 206 Deletion Series:

The DNA sequences specified below were amplified by PCR and subcloned into vector p206 TAP-GUS (FIG. 12(A); −206TAP). The existing restriction endonucleases EcoRI and NcoI were used to excise the 206TAP-intron region from the promoter sequence. The p206 TAP-GUS sequence was used as template for each PCR reaction to generate a deletion series TAP 150, TAP 140, TAP 130, TAP 120, TAP 110, TAP 100, and TAP 50. A GUS antisense (GUS AS) primer and matching TAP targeted sequence to which EcoRI and KpnI restriction endonucleases were added was used to generate TAP deletion sequences with an exception of TAP110 in which EcoRI and Nsi restriction sites were used. PCR product was digested with EcoRI/NcoI and subcloned into the vector (p206TAP).

206 Deletion Series Primers: (Restriction Endonuclease Sites Underlined)

TAP 150: TTT GAA TTC GGT ACC TCC ACG CAT CTC TCG CTC G (SEQ ID NO:27)

TAP 140: TTT GAA TTC GGT ACC CGC ATC TCT CGC TCG AAC (SEQ ID NO:28)

TAP 130: TTT GAA TTC GGT ACC GCT CGA ACC CCT ATT TAA (SEQ ID NO:29)

TAP 120: TTT GAA TTC GGT ACC CTA TTT AAG CCC CTC CC (SEQ ID NO:30)

TAP 110: TTT GAA TTC ATG CAT CCC TCC ATT CTT CCC TAC (SEQ ID NO:31)

TAP 100: TTT GAA TTC GGT ACC TTC CCT ACA TTC TCC ACA CAA CC (SEQ ID NO:32)

TAP 50: TTT GAA TTC GGT ACC ATC ACT ACG TAA TAC GGT GC (SEQ ID NO:33)

GUS AS; TCA COG GTT GGG GGT TCT AC (SEQ ID NO:34)

−130 to −120/−113 to −116 Mutation

This mutation was prepared as the −113 to −116 region was observed to be AT rich, therefore, this region was modified to determine the effect of this sequence on TAP activity. In order to introduce the modifications into this region, other restriction sites were introduced in the −120 to −120 region as described below.

The mutation was generated by PCR in two steps:
1. The first PCR primers (I) contained GUS antisense (GUS AS) and 110TAP with EcoRI and Nsi ends as follows:

5′—TTGAA TTC ATG CATCAC TAT ATA GCC CCT CC—3′ (bold=EcoRI and Nsi respectively; SEQ ID NO: 35)

2. The second primers (II) were 120TAP antisense with Pst end+M13 forward PCR.

5—'TTTT CTG CAG GGG TTC GAG CGA GAG ATG CG—3′ (bold=PstI; SEQ ID NO: 36)

The PCR products from primers I and II were excised with NsiI/NcoI and Pst/EcoRI respectively and ligated. The resulting EcoRI/NcoI construct was subsequently subcloned into p206TAP digested with Nsi/Nco, The resultant construct comprised the dicot TATA consensus sequence along with extra nucleotides associated with the introduction of the PstI and Nsi restriction sites.

−120 to −80 Deletions

The deletion was generated by PCR in two steps.
1. The first PCR product was generated by GUS antisense primer (GUS AS) and matching sequence of −80TAP with Nsi restriction endonuclease as follows:

5—'TTT ATG CAT ACC ACG AGT TGC TCA TCT CC-3′ (bold=NsiI; SEQ ID NO:37)

2. The second primers were −120TAP antisense (as described above)+M13 forward PCR.

The PCR products obtained from 1 and 2, above were digested with Nsi and Pst, respectively and ligated. The resulting construct was excised with EcoRI/Nco and subcloned into p206TAP.

2) Preparation of New TAP Regulatory Region Constructs

A series of mutations within the TAP nucleotide sequence were prepared (TAP 1–TAP 5; see FIGS. 13(A) and (C)) by PCR using primers pr1–5 and the pr6 as the primers (listed in Table 7) and the plasmid −206TAP-GUS as the template. The PCR product was digested with NcoI and KpnI, and the resulting fragment was used to replace the NcoI and KpnI fragment in −206TAP-GUS.

Chimeric TAP Constructs

To generate GCC(4)TAP and G(5)TAP constructs (see FIG. 13(B)), a 46-bp fragment:
AATTGCCGCCACTAGCCGCCGACCGA GCCGCCAAGAGCCGCCAGCT (SEQ ID NO:38)
containing four GCC boxes (GCCGCC), or a 54-bp fragment:
AATTGCCGCCACGTGCCGCCACGTGCCGCCACGT GCCGCCACGTGCCGCCAGCT (SEQ ID NO: 39),
containing five G-boxes (GCCGCCACGT) was ligated into the EcoRI and PstI site located upstream of the −206TAP-GUS construct.

The (BST2)TAP constructs (FIG. 13(B)) were generated by PCR using pr7 and pr8 (Table 7) as the primers and the −394 to −62 fragment of T1275 regulatory region (see U.S. Pat. No. 5,824,872) as the template. The PCR product was digested with EcoRI and SacI, and the resulting fragment was ligated into the EcoRI and PstI site located upstream of the −206TAP-GUS construct.

TABLE I

Oligonucleotides used in PCR to create constructs

| Primer | Sequence |
| --- | --- |
| pr1 | ctaggatcca atccttcgga agggaaaaag (SEQ ID NO:14) |
| pr2 | agcttgggcc cgaaggatcc agggaaaaag aaaaaggggt c (SEQ ID NO:15) |
| pr3 | agcttgggcc atccttcgga ggatccccct aaaaaggggt cctgctgcac (SEQ ID NO:16) |
| pr4 | agcttgggcc atccttcgga agggaaaaag cccggatccg cctgctgcac cagcgactaa (SEQ ID NO:17) |
| pr5 | agcttgggcc atccttcgga agggaaaaag aaaaaggggt aagtggatcc cagcgactaa accatccacg (SEQ ID NO:18) |
| pr6 | atataagctttggggtttctacaggacg (SEQ ID NO:19) |
| pr7 | cggaattcgaaagcttgcatgcctgcagg (SEQ ID NO:20) |
| pr8 | aattgagctcatgcatggatcaaaagggaaac (SEQ ID NO:21) |

Preparation of Test Material and Transient Assay Analysis

Corn type II callus was grown in vitro in N6 basal salt medium (Sigma USA) supplemented with 1.4 g/l proline, 0.7 g/l aspergine, 0.3 g/L glutamine, 1.0 mg/l 2,4-D, B5 vitamins (Gamborg, O. L, et al. (1968), J. Exp. Res. 50, 151–158) and 2% sucrose w/v, (pH 5.8). The petri dishes were kept in dark at 22° C. and the growth medium was replaced with fresh medium at interval of 34 weeks. The calli were transfer to fresh growth medium at least 5–7 days prior to gene transfer via particle gun delivery system.

Fresh callus tissue for bombardment was placed on 1 cm² filter paper on callus growth medium as described above. 2.5 ug of test plasmid and luciferase DNA was precipitated onto gold microprojectiles using 25 uL microprojectile solution (1.78 mg of 1 uM gold in 25 ul glycerol), 25 uL of 2.5M calcium chloride and 10 uL of 100 mM spermidine, rinsed with ethanol and re-suspended in 40 uL of 100% ethanol. 10 uL of solution was spotted onto the center of each macro-carrier and used to shoot callus tissue using 1 100 psi rupture disks in the PDS-1000 BioRad Gene Gun. The callus was kept in dark at 22 C. for 48 hours prior to GUS assay.

To assay GUS activity the callus was harvested and frozen in liquid nitrogen. The tissue was ground in extraction buffer containing of 100 mM Potassium phosphate (pH 7.8), 1 mM 1,2-diaminocyclohexane-N,N,N,N-tetraacetic acid, 10% glycerol, 0.5% Triton X-100 and 7 mM 2-mercaptoethanol. The extract was homogenized for 1 minute using a hand held homogenizer and centrifuged for 15 min at 4° C. and the supernatant was used for GUS assays.

For fluorometric GUS assays (Jefferson, R. A. (1987) Plant Mol. Biol. Rep. 5: 387–405), 170 µL of the crude extract was incubated at 37° C. with 1 mM 4-methylumbelliferyl glucuronide in 0.3 mL of GUS assay buffer (50 mM NaPO4, pH 7.0, 10 mM EDTA, 0.1% [v/v] Triton X-100, 10 mM β-mercaptoethanol). After 0, 0.5, 1 and 2 h of incubation, 0.1-mL aliquots were removed and added to 1.9 mL of 0.2 M Na₂CO₃ to terminate the reaction. GUS activity was expressed as picomoles of 4-methylumbelliferone per milligram of protein per minute.

For histochemical GUS assay, tissue was incubated in a 0.5 mg/ml solution of 5-bromo-4-chloro-indolyl β-D-glucuronide in 100 nM sodium phosphate buffer, pH 7.0, infiltrated in a vacuum for half an hour and incubated at 37° C. overnight. Following the incubation, tissue was washed in 70% ethanol.

For luciferase assays, 20 µl of cell extract was placed in a luminometer cuvette, and then 200 µl of luciferase assay buffer (25 mM Tricine, pH 7.8, pH 7.8, 15 mM MgCl₂, 5 mM ATP, and 1 mg/ml BSA) was added. The mixture was allowed to equilibrate to room temperature (about 15 min). Placement of the cuvette in the counting chamber of a luminonieter automatically activated the machine and 100 µl of 500 µM luciferin was injected into the cuvette to start the reaction. The emitted photons were integrated over a 10-s period and expressed as relative light units/10 s. Correction for differences in sample variability and transfection efficiency was done by normalization of the GUS activity with luciferase activity in the light unit, yielding the GUS to luciferase ratio of each sample.

Wheat callus production was induced by placing 14–20 day old embryos of the variety SuMais 3, embryo side down on callus induction Murashige and Skoog (MS) medium (Murashige and Skoog 1962) with 2,4-D, (Weeks J. T. e al. (1993). Pl. Phys. 102: 1077–1084; Weeks, J. T. (1995), Stable transformation of wheat by microprojectile bombardment. In: Gene transfer to plants. Eds. I Potrykus and G. Spangenberg. Springer. pp. 157–161). When significant callus production was observed within 5 to 31 days these were crushed onto filter paper, 4 embryos per plate and transferred to fresh media in preparation for bombardment (Harvey, A., L. et al. (1990), Plant Cell Tissue and Organ Culture. 57: 153–156).

Tobacco leaves were harvested from in vitro cultures maintained on MS medium (Murashige, T and F. Skoog. 1962. Physiol. Plant. 15: 473–497). Leaves selected for bombardment were of uniform size and colour which were then preincubated on MS medium containing NAA and BA overnight prior to bombardment.

Construct DNA was extracted and purified, and each sample was diluted to a concentration of 1 µg/µl for use in the bombardment protocol. Prior to bombardment tungsten particles were coated with transforming DNA by adding the following chilled sterile solutions in order 5 µL DNA, 25 µL 2.5 M CaCl₂ and 5 µL spermidine. Wheat callus and tobacco leaf tissue was bombarded with 2 µL of the DNA/tungsten solution. The settings were 100 psi pressure for wheat and 150 psi pressure for tobacco with the tissue sitting at position 10 in the particle bombardment device (Brown et al. 1994, Buckley et al. 1995).

Tissue was incubated in a growth chamber overnight following bombardment.

For histochemical analysis the tissue was covered with 3 mL GUS incubation buffer and left overnight in the dark at 37° C. Visual counts were made of positive GUS staining using a dissecting microscope.

For fluorometric analysis tissue was collected and ground in liquid nitrogen and either stored at −80° C. or immediately extracted folowing protocols modified from Gartland et al. (Gartland, M. A., et. al. (1995), Fluorometric GUS analysis for transformed plant material. In: Methods in Molecular Biology, Vol. 44: Agrobacterium Protocols. Eds: K. M. A. Gartland and M. R. Davey Humana Press Inc., Totowa N.Y. pp 195–199) and Vitha et al. (Vitha, S. K et. al. (1993), Biologia Plantarum 35(1): 151–155). Fluorometric readings were taken on a RF-Mini 150 Recording Fluorometer, and protein content was assessed using a Bradford assay read in the BioRad Model 2550 EIA Reader. Fluorometric data was analysed using Lotus 123 and Microsoft Excel.

Figure 12B:
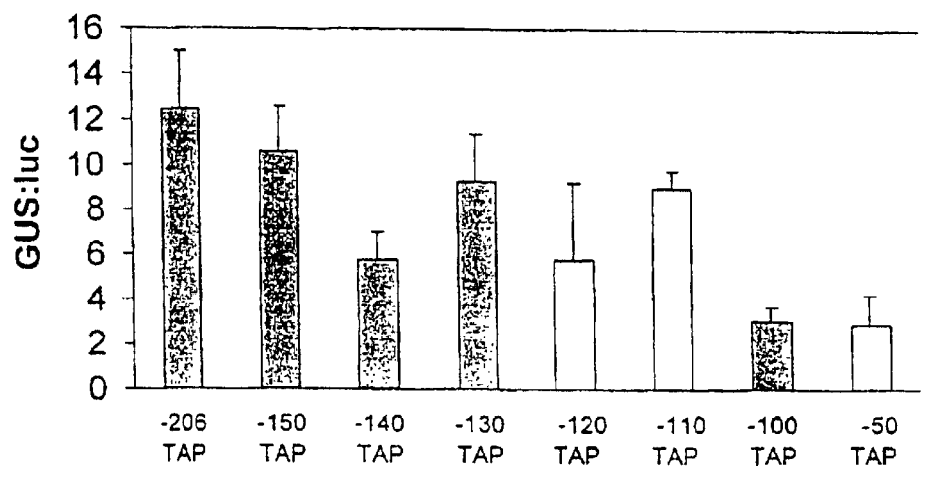
FIG. 12(B) shows the activity of the constructs outlined in FIG. 12(A) within corn callus as determined using transient expression analysis.

Results from transient expression analysis of the constructs shown in FIG. 12(A) in corn callus is shown in FIG. 12(B). Deletions from −206 to about −110 of the TAP regulatory region did not have any appreciable effect of the activity of the p206Ltp regulatory region. However, the region between −100 and −110 (see GUS activity associated with the −110 TAP and −100 TAP constructs) was essential for high expression levels since deletion of this region resulted in a dramatic decrease in regulatory region activity as indicated by GUS analysis. Similar results were observed using a histochemical analysis of bombarded corn callus, where deletion of −100 to −50 region resulted in no regulatory region activity (data not shown).

Transient analysis of the −150 TAP, −100 TAP and −50 TAP deletion constructs in wheat culture is shown in FIG. 14(A), and in tobacco culture is shown in FIG. 14(C). Analysis of the −150 TAP construct in wheat, along with two other mutations, −130 to −120/−113 to −116 mutation, and the −120 to −80 deletion construct are shown in FIG. 14(B). In wheat, high levels of regulatory region activity are still observed with the −150 TAP construct (FIG. 14(B)), while there is a dramatic decreased in the activity of the TAP regulatory element with the removal of the −150 region as indicated with the activity associated with the −100 TAP construct compared with the −150 TAP construct (FIG. 14(A)), or the −120 to −80 region (FIG. 14(B)), suggesting that key regulatory elements reside within this region (i.e. the −150 to −100-region). The −113 to −116 region is AT rich region, and substituting several bases within this region (as in the case of the −130 to −120/−113 to −116 mutation construct; see above), resulted in a decrease in activity (FIG. 14(B)). These results collectively indicate that the −150 to −100 region is required for TAP regulatory region activity in cereals, for example wheat and corn.

Similar analysis of the deletion constructs in tobacco culture demonstrate that a significant amount of activity is associated with the −150 TAP, −100 TAP and the −50 TAP constructs, and that there is no loss of activity with the removal of the −150 to −100, or −50 region. These data suggests that the sequence from −50, which includes the intron (see FIG. 12(A); the intron used in these constructs is the ADH 156 intron), exhibits regulatory region activity in dicots.

Analysis of the mutation constructs disclosed in FIGS. 13(A) and (B) in wheat is shown in FIG. 14(A). The TAP 1 to TAP 4 constructs all exhibit a large increase in activity when compared with the activity associated with the p206Ltp (TAP) construct. Similarly, chimeric regulatory elements comprising TAP and G(5), or (Bst)$_2$ also exhibit an increase in regulatory region activity (FIG. 14(A)). Collectively these results demonstrate that substitutions or additions to the Ltp regulatory region, preferably the p206Ltp region, result in increased activity when determined with a monocot plant.

Analysis of the mutation constructs disclosed in FIGS. 13(A) and (B) in tobacco is shown in FIG. 14(C). The TAP 1 to TAP 5 constructs exhibit a significant and similar level of regulatory region activity. Chimeric regulatory elements comprising (Bst)$_2$ TAP, GCC (4) TAP or G(5) TAP also exhibit significant regulatory region activity (FIG. 14(C)). Collectively these results demonstrate that substitutions or additions to the Ltp regulatory region, preferably the p206Ltp region, result in increased activity when determined with a monocot plant.

All citations are herein incorporated by reference.

The present invention has been described with regard to preferred embodiments. However, it will be obvious to persons skilled in the art that a number of variations and modifications can be made without departing from the scope of the invention as described herein.

What is claimed is:

1. A regulatory element comprising; a nucleotide sequence of SEQ ID NO:23 or a nucleotide sequence that hybridizes to the nucleotide sequence of SEQ ID NO:23 under the following conditions: hybridization in 5×SSC and 50% formamide at 42° C.; and washing from about 0.5×SSC to about 0.2×SSC at 65° C., and wherein the hybridizing nucleotide sequence exhibits regulatory element activity.

2. The regulatory element of claim 1, wherein said regulatory element is 687LtpW1.

3. The regulatory element of claim 1, wherein said regulatory element is 473LtpW1.

4. A dicotyledonous plant comprising a gene construct, said gene construct comprising:
  i) a nucleotide sequence of SEQ ID NO:23 or a nucleotide sequence that hybridizes to the nucleotide sequence under the following conditions: hybridization in 5×SSC and 50% formamide at 42° C.; and washing from about 0.5×SSC to about 0.2×SSC at 65° C., and wherein the hybridizing nucleotide sequence exhibits regulatory element activity; and
  ii) a gene of interest in operative association with said nucleotide sequence.

5. A monocotyledonous plant comprising a gene construct, said gene construct comprising:
  i) a nucleotide sequence of SEQ ID NO:23 or a nucleotide sequence that hybridizes to the nucleotide sequence under the following conditions: hybridization in 5×SSC and 50% formamide at 42° C.; and washing from about 0.5×SSC to about 0.2×SSC at 65° C., and wherein the hybridizing nucleotide sequence exhibits regulatory element activity; and
  ii) a gene of interest in operative association with said nucleotide sequence.

6. The regulatory element of claim 1, wherein said regulatory element is a chimeric regulatory element, comprising an exogenous regulatory element selected from the group consisting of an enhancer element and a silencer element.

7. The regulatory element of claim 6, wherein said exogenous regulatory element is an enhancer element.

8. The regulatory element of claim 7, wherein said enhancer element is selected from the group consisting of a 35S enhancer, an actin enhancer, a BstYI fragment of T1275, one or more GCC box elements, and one or more Gbox elements.

9. A gene construct comprising the regulatory element of claim 1, in operative association with a gene of interest.

10. A plant cell culture comprising the gene construct of claim 9.

11. A plant comprising the gene construct of claim 9.

12. A seed comprising the gene construct of claim 9.

13. The plant of claim 11, wherein the plant is a monocotyledonous plant.

14. The plant of claim 11, wherein the plant is a dicotyledonous plant.

15. A method of expressing a gene of interest within a plant comprising:
  i) operatively linking a gene of interest for which expression is desired with the regulatory element of claim 1 to produce a gene construct; and ii) introducing said gene construct into said plant and allowing for expression of said gene of interest.

16. The method of claim 15 wherein said plant is a monocotyledonous plant.

17. The method of claim 16 wherein said plant is a dicotyledonous plant.

* * * * *